United States Patent [19]

Itoh et al.

[11] 4,242,507
[45] Dec. 30, 1980

[54] SULFONIC ACID ESTERS

[75] Inventors: Masumi Itoh, Takatsuki; Jiyoji Notani, Kawanishi, both of Japan

[73] Assignee: Fujisawa Pharmaceutical Co., Ltd., Osaka, Japan

[21] Appl. No.: 880,436

[22] Filed: Feb. 23, 1978

Related U.S. Application Data

[63] Continuation of Ser. No. 662,033, Feb. 27, 1976, abandoned, which is a continuation-in-part of Ser. No. 465,125, Apr. 29, 1974, abandoned.

[51] Int. Cl.³ .................... C07D 249/18; C07D 253/08
[52] U.S. Cl. ............................ 542/427; 260/112.5 R; 544/28; 544/183; 544/366; 546/271; 548/253; 548/259
[58] Field of Search .................... 260/308 B; 544/183; 542/427; 546/271; 548/259

[56] References Cited
U.S. PATENT DOCUMENTS 3,700,604  10/1972  Metil .................................. 252/426

OTHER PUBLICATIONS

Birchall et al., *J. Chem. Soc.*, C1970, (11), 1519–1523.
Campbell et al., *J. Chem. Soc.*, C1969, (5), 742–747.

*Primary Examiner*—Paul M. Coughlan, Jr.
*Attorney, Agent, or Firm*—Bierman & Bierman

[57] ABSTRACT

A novel process for the amidation or esterification which comprises reacting a compound having a carboxy group with a compound having an amino or imino group which can be acylated or with a compound having a hydroxy group in the presence of a sulfonic acid ester of the formula:

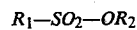

$$R_1-SO_2-OR_2$$

wherein $R_1$ is an organic group and $R_2O-$ is a residue of a strongly acidic N-hydroxy compound as a condensation agent, and a novel sulfonic acid ester useful as such a condensation agent and a process for the preparation thereof.

57 Claims, No Drawings

SULFONIC ACID ESTERS

This is a Rule 60 continuation application of Ser. No. 662,033 filed Feb. 27, 1976, now abandoned, which is a continuation-in-part application of Ser. No. 465,125 filed Apr. 29, 1974, now abandoned, and which claims the priority of Japanese Patent Application Nos. 48736/1973 filed Apr. 28, 1973, 75460/1973 filed July 3, 1973, 75461/1973 filed July 3, 1973, 91139/1973 filed Aug. 13, 1973, and 25866/1974 filed Mar. 4, 1974.

The present invention relates to a novel process for the amidation and esterification by using a novel condensation agent, novel compounds useful as the condensation agent and a process for the preparation thereof. More particularly, it relates to a novel process for the amidation or esterification which comprises reacting a compound having a carboxy group with a compound having an amino or imino group which can be acylated or with a compound having a hydroxy group in the presence of a sulfonic acid ester of the formula:

$$R_1-SO_2-OR_2 \quad (I)$$

wherein $R_1$ is an organic group and $R_2O-$ is a residue of a strongly acidic N-hydroxy compound as a condensation agent, and further, it relates to a novel sulfonic acid ester useful as such a condensation agent and a process for the preparation thereof.

According to the present invention, it has been newly found that the sulfonic acid esters of the formula (I) are excellent as a condensation agent in amidation or esterification reaction, and particularly, the sulfonic acid esters (I) have various advantages that they are easily handled because the esters (I) are generally stable crystals and hardly hydrolyzed by contacting with water and further have no danger such as dermatitis or burn as in the conventional condensation agents, and that the amidation or esterification reaction may be easily carried out under mild conditions without undesirable side reaction to give the desired amide or ester compound in high yield and within comparatively shorter time, which means that the present condensation agent may also be applied to the production of unstable and hardly prepared compounds, and further that the starting compounds in amidation may be directly reacted to give the desired amide compound, i.e. neither the carboxy group nor the amino or imino group of the starting compounds has to be activated prior to the addition thereof to the reaction system.

The sulfonic acid esters of the present invention has the foregoing general formula (I). The organic group for $R_1$ in the formula (I) includes a substituted or unsubstituted aliphatic hydrocarbon group, a substituted or unsubstituted aryl group and a substituted or unsubstituted heterocyclic group.

The substituted or unsubstituted aliphatic hydrocarbon group includes saturated or unsaturated hydrocarbon groups which may be branched or cyclic. The examples of the aliphatic hydrocarbon groups may be an alkyl (e.g. methyl, ethyl, propyl, isopropyl, butyl, isobutyl, pentyl, isopentyl or hexyl), an alkenyl (e.g. vinyl, 2-propenyl, 1-isopropenyl, 3-butenyl or 2-methyl-2-propenyl), an alkynyl (e.g. ethynyl or 2-propynyl), a cycloalkyl (e.g. cyclopropyl, cyclobutyl, cyclopentyl or cyclohexyl), a cycloalkenyl (e.g. cyclopropenyl, cyclobutenyl, cyclopentenyl or cyclohexenyl), a bicycloalkyl (e.g. 1,7,7-trimethylbicyclo[2,2,1]heptyl), a cycloalkylalkyl (e.g. cyclopropylmethyl, cyclobutylmethyl, cyclohexylmethyl or 2-cyclohexylethyl), a cycloalkylalkenyl (e.g. 2-cyclohexylvinyl or 3-cyclohexyl-2-propenyl), a cycloalkenylalkyl (e.g. cyclopropenylmethyl, 2-cyclobutenylethyl or cyclohexenylmethyl), a cycloalkenylalkenyl (e.g. 2-cyclohexenylvinyl or 3-cyclohexenyl-2-(2-methylpropenyl)), a bicycloalkylalkyl (e.g. 7,7-dimethylbicyclo[2,2,1]heptylmethyl or 7,7-dimethyl-2-bicyclo[2,2,1]heptylethyl) or the like.

The aliphatic hydrocarbon group may have one or more substituents at optional positions. The substituents include every kinds of substituents unless they give any undesirable effect to the reaction. The examples of the substituents may be an alkoxy (e.g. methoxy, ethoxy, propoxy, or isopropoxy), an alkylthio (e.g. methylthio, ethylthio, propylthio or isopropylthio), amino, mercapto, nitro, cyano, a halogen (e.g. chlorine, fluorine or bromine), oxo, carboxy, sulfo, a halosulfonyl (e.g. chlorosulfonyl, bromosulfonyl or fluorosulfonyl), hydroxy, hydroxyamino, a mono- or dialkylamino (e.g. mono- or dimethylamino, mono- or diethylamino, mono- or dipropylamino, or mono- or diisopropylamino), an aryl, an acyl, a heterocyclic group, or the like.

The aryl group being one of the substituents of the aliphatic hydrocarbon group includes phenyl, tolyl, xylyl, mesityl, cumenyl and naphthyl which may be substituted with one or more groups at optional positions unless they give any undesirable effect to the reaction. The examples of the substituents may be an alkoxy (e.g. methoxy, ethoxy or propoxy), an alkylthio (e.g. methylthio or ethylthio), amino, mercapto, nitro, cyano, a halogen (chlorine, fluorine or bromine), carboxy, sulfo, a halosulfonyl (e.g. chlorosulfonyl, bromosulfonyl or fluorosulfonyl), hydroxy, hydroxyamino, a mono- or dialkylamino (e.g. mono- or dimethylamino, or mono- or diethylamino), or the like. Further, the examples of the substituted aryl group may be 4-methoxypheny, 4-methylthiophenyl, 4-aminophenyl, α-aminonaphthyl, 2-amino-3-hydroxyphenyl, 4-mercaptophenyl, 4-nitrophenyl, 4-cyanophenyl, 4-chlorophenyl, 4-methoxycarbonylphenyl, 4-sulfophenyl, 4-hydroxyphenyl, 4-hydroxyaminophenyl, 4-dimethylaminophenyl, or the like.

The acyl group being one of the substituents of the aliphatic hydrocarbon group means the remaining group of an organic carboxylic acid or sulfonic acid, from which a hydroxy group is removed, that is, it includes an aliphatic acyl, an aromatic group-containing acyl and a heterocyclic group-containing acyl. The aliphatic acyl may be a saturated or unsaturated alkanoyl or a saturated or unsaturated alkanesulfonyl which may be branched or cyclic. The examples of the aliphatic acyl may be formyl, acetyl, propionyl, butyryl, isobutyryl, valeryl, isovaleryl, pivaloyl, acryloyl, crotonoyl, 2-methylacryloyl, cyclopentylcarbonyl, cyclohexylcarbonyl, cycloheptylcarbonyl, succinyl, cyclopentylacetyl, cyclohexylacetyl, cycloheptylacetyl, cyclohexylpropionyl, cycloheptylpropionyl, dihydrobenzoyl, 2,4,6-cycloheptatrienylacetyl, dihydrophenylacetyl, methanesulfonyl, ethanesulfonyl, propanesulfonyl, butanesulfonyl, vinylsulfonyl, allylsulfonyl, ethynylsulfonyl, cyclopropylsulfonyl, cyclobutylsulfonyl, cyclopentylsulfonyl, cyclohexylsulfonyl, or the like. The carbon atom in the alkyl moiety of the above saturated or unsaturated alkanoyl may be replaced by oxygen or sulfur atom. The examples of such acyl group may be methoxyacetyl, methylthioacetyl, 2-propenylthioacetyl, cyclohexylthioacetyl, cyclohexyloxyacetyl, dihydrophenoxyacetyl, dihydrophenylthioacetyl, or the like. The aliphatic acyl includes also an esterified carboxy group, such as an alkoxycarbonyl (e.g. methoxycarbonyl, ethoxycarbonyl, propoxycarbonyl, isopropoxycarbonyl or butoxycarbonyl), an aralkoxycarbonyl (e.g. benzyloxycarbonyl or phenethyloxycarbonyl), or the like. The examples of the aromatic group-containing acyl may be an aroyl (e.g. benzoyl, toluoyl, naphthoyl, α-methylnaphthoyl, phthaloyl or tetrahydronaphthoyl), an aralkanoyl (e.g. phenylacetyl, phenylpropionyl, phenylbutyryl, tolylacetyl, xylylacetyl, naphthylacetyl or tetrahydronaphthylacetyl), an arylsulfonyl (e.g. benzenesulfonyl, naphthylsulfonyl or p-toluenesulfonyl), an aralkylsulfonyl (e.g. benzylsulfonyl or phenethylsulfonyl), or the like. The carbon atom in the alkyl moiety of the above aralkanoyl may be replaced by oxygen or sulfur atom. The examples of such acyl group may be phenoxyacetyl, phenylthioacetyl, 2-phenoxypropionyl, 2-phenoxybutyryl, or the like. The heterocyclic group of the heterocyclic group-containing acyl may be a saturated or unsaturated monocyclic or polycyclic heterocyclic group which contains at least one hetero atom selected from oxygen, sulfur, nitrogen or the like. The examples of the heterocyclic group-containing acyl may be a heterocyclic carbonyl and heterocyclic sulfonyl group, which contain a heterocyclic group, such as an unsaturated 3 to 8-membered heteromonocyclic containing a sulfur atom (e.g. thienyl), an unsaturated condensed-heterocyclic containing a sulfur atom (e.g. benzothienyl), an unsaturated 3 to 8-membered heteromonocyclic containing an oxygen atom (e.g. furyl, pyranyl or 5,6-dihydro-2H-pyranyl), an unsaturated condensed-heterocyclic containing an oxygen atom (e.g. isobenzofuranyl, chromenyl or xanthenyl), an unsaturated 3 to 8-membered heteromonocyclic containing 1 to 4 nitrogen atom(s) (e.g. 2H-pyrrolyl, 3H-pyrrolyl, pyrrolyl, pyrrolinyl, imidazolyl, pyrazolyl, pyridyl, pyrimidinyl, pyradinyl, pyridazinyl, diazolyl, triazolyl or tetrazolyl), a saturated 3 to 8-membered heteromonocyclic containing 1 to 2 nitrogen atom(s) (e.g. pyrrolidinyl, imidazolidinyl, piperidyl or piperazinyl), an unsaturated condensed-heterocyclic containing 1 to 3 nitrogen atom(s) (e.g. indolyl, isoindolyl, indazolyl, quinolyl, isoquinolyl, benzotriazolyl or benzimidazolyl), an unsaturated 3 to 8-membered heteromonocyclic containing an oxygen atom and 1 to 3 nitrogen atom(s) (e.g. oxazolyl, isoxazolyl or oxadiazolyl), a saturated 3 to 8-membered heteromonocyclic containing 1 to 2-oxygen atom(s) and 1 to 2 nitrogen atom(s) (e.g. sydnonyl), an unsaturated condensed-heterocyclic containing an oxygen atom and 1 to 2 nitrogen atom(s) (e.g. benzoxazolyl or benzoxadiazolyl), an unsaturated 3 to 8-membered heteromonocyclic containing a sulfur atom and 1 to 3 nitrogen atom(s) (e.g. thiazolyl, isothiazolyl or thiadiazolyl), an unsaturated condensed-heterocyclic containing a sulfur atom and 1 to 2 nitrogen atom(s) (e.g. benzothiazolyl or benzothiadiazolyl), or the like, and further may be an alkanoyl (e.g. acetyl, propionyl, butyryl, isobutyryl, valeryl, isovaleryl, pivaloyl, acryloyl, crotonyl or 2-methylacryloyl) substituted with the above listed heterocyclic group, a heterocyclic oxy group, a heterocyclic thio group, a heterocyclic amino group or an N-alkyl heterocyclic amino group, for instance, 1H- or 2H-tetrazolylacetyl, tetrazolylpropionyl, thienylacetyl, thienylpropionyl, furylacetyl, piperazinylacetyl, pyrrolidinylacetyl, pyrrolidinylpropionyl, pyridylpropionyl, thiadiazolylacetyl, benzothiazolylacetyl, sydnonylacetyl, oxazolylacetyl, benzoxazolylacetyl, or the like. The carbon atom in the alkyl moiety of the alkanoyl group contained in the heterocyclic group-containing acyl may be replaced by oxygen or sulfur atom, for instance, there may be pyridylmethoxycarbonyl, tetrazolylmethylthioacetyl, or the like.

The aliphatic acyl, aromatic group-containing acyl and heterocyclic group-containing acyl may have one or more substituents at the optional positions. The substituents include every kinds of substituents unless they give any undesirable effect to the reaction. The examples of the substituents may be an alkyl (e.g. methyl, ethyl, propyl or isopropyl), an alkenyl (e.g. 1-propenyl or 2-propenyl), a cycloalkyl (e.g. cyclopropyl, cyclopentyl, cyclohexyl or cycloheptyl), an alkoxy (e.g. methoxy, ethoxy, propoxy or isopropoxy), an alkylthio (e.g. methylthio, ethylthio, propylthio or isopropylthio), an aryl (e.g. phenyl, tolyl, xylyl or mesityl), an aralkyl (e.g. benzyl or phenethyl), amino, mercapto, nitro, cyano, a halogen (e.g. chlorine, fluorine or bromine), carboxy, sulfo, a halosulfonyl (e.g. chlorosulfonyl, bromosulfonyl or fluorosulfonyl), hydroxy, hydroxyamino, a mono- or dialkylamino (e.g. mono- or dimethylamino, mono- or diethylamino, mono- or dipropylamino, or mono- or diisopropylamino), or the like. The examples of the aliphatic acyl, aromatic group-containing acyl and heterocyclic group-containing acyl which have such substituents may be chloroacetyl, chloromethylsulfonyl, cyanoacetyl, 2-chloropropionyl, trifluoroacetyl, α-aminophenylacetyl, α-hydroxyphenylacetyl, p-hydroxyphenylacetyl, 2-amino-2-(5,6-dihydro-2H-pyran-3-yl)acetyl, 2-amino-2-(p-hydroxyphenyl)acetyl, 2,6-dimethoxybenzoyl, α-hydroxythienylacetyl, 3-phenyl-5-methyl-4-oxazolylcarbonyl, 3-(2-chlorophenyl)-5-methyl-4-oxazolylcarbonyl, 3-(2,6-dichlorophenyl)-5-methyl-4-oxazolylcarbonyl, 3-(2-chloro-6-fluorophenyl)-5-methyl-4-oxazolylcarbonyl, or the like.

The heterocyclic group being one of the substituents of the aliphatic hydrocarbon group includes aliphatic or aromatic mono- or polycyclic heterocyclic groups which contain at least one hetero atom selected from oxygen, sulfur, nitrogen or the like. The examples of the heterocyclic groups may be an unsaturated 3 to 8-membered heteromonocyclic containing a sulfur atom (e.g. thienyl), an unsaturated condensed-heterocyclic containing a sulfur atom (e.g. benzothienyl), an unsaturated 3 to 8-membered heteromonocyclic containing an oxygen atom (e.g. furyl), an unsaturated 3 to 8-membered heteromonocyclic containing 1 to 4 nitrogen atom(s) (e.g. pyrrolyl, imidazolyl, pyridyl, pyrimidinyl, triazolyl or tetrazolyl), a saturated 3 to 8-membered heteromonocyclic containing 1 to 2 nitrogen atom(s) (e.g. pyrrolidinyl, piperidyl, piperidino, homopiperidyl or piperazinyl), an unsaturated condensed-heterocyclic containing 1 to 3 nitrogen atom(s) (e.g. indolyl, isoindolyl, quinolyl, isoquinolyl or benzimidazolyl), an unsaturated 3 to 8-membered heteromonocyclic containing an oxygen atom and 1 to 3 nitrogen atom(s) (e.g. oxazolyl, isoxazolyl, oxadiazolyl or oxatriazolyl), a saturated 3 to 8-membered heteromonocyclic containing 1 to 2 oxygen atom(s) and 1 to 2 nitrogen atom(s) (e.g. morpholino or sydnonyl), an unsaturated condensed-heterocyclic containing an oxygen atom and 1 to 2 nitrogen atom(s) (e.g. benzoxazolyl), an unsaturated 3 to 8-membered heteromonocyclic containing a sulfur atom and 1 to 3 nitrogen atom(s) (e.g. thiazolyl, thiadiazolyl or thiatrizolyl), an unsaturated condensed-heterocyclic containing a sulfur atom and 1 to 2 nitrogen atom(s) (e.g. benzothiazolyl or benzothiazolinyl), or the like. These heterocyclic groups may be substituted with one or more substituents which do not give any undesirable effects to the reaction, such as an alkyl (e.g. methyl or ethyl), an alkoxy (e.g. methoxy or ethoxy), a halogen (e.g. fluorine, chlorine or bromine), oxo, amino, nitro, an aryl (e.g. phenyl, tolyl or xylyl), a substituted aryl (e.g. chlorophenyl or nitrophenyl), an aralkyl (e.g. benzyl or phenethyl), or the like.

When the substituents of the aliphatic hydrocarbon group are amino, hydroxy, mercapto, carboxy and sulfo, or when the aryl group, acyl group or heterocyclic group being one of the substituents of the aliphatic hydrocarbon group contains amino, hydroxy, mercapto, carboxy or sulfo substituents, these substituents may be protected by an appropriate protecting group.

The protecting group for amino group includes every kinds of the conventional amino protecting groups, for instance, the acyl group as mentioned above as the substituent of the aliphatic hydrocarbon group (i.e. an aliphatic acyl, an aromatic group-containing acyl or a heterocyclic group-containing acyl), methoxycarbonyl, ethoxycarbonyl, propoxycabonyl, tertiary butoxycarbonyl, tertiary amyloxycarbonyl, benzyloxycarbonyl, p-nitrobenzyloxycarbonyl, or the like. Furthermore, the amino group may be protected by two carboxy groups, for instance, the amino group combines with phthalic acid to form a phthalimido bond.

The protecting group for hydroxy and mercapto group includes every kinds of the conventional hydroxy or mercapto protecting groups, for instance, the acyl group as mentioned above as the substituent of the aliphatic hydrocarbon group (i.e. an aliphatic acyl, an aromatic group-containing acyl or a heterocyclic group-containing acyl), methyl, ethyl, propyl, phenyl, tolyl, xylyl, benzyl, phenethyl, methoxymethyl, or the like.

The protecting group for carboxy and sulfo group includes every kinds of the conventional carboxy or sulfo protecting groups, for instance, the hydrogen of the hydroxy group in the carboxy or sulfo group may be substituted by methyl, ethyl propyl, isopropyl, butyl, benzyl, p-nitrobenzyl, benzoylmethyl, acetylmethyl, p-nitrobenzoylmethyl, p-bromobenzoylmethyl, p-methanesulfonylbenzoylmethyl, trichloroethyl, tribromoethyl, acetoxymethyl, propionyloxymethyl, pivaloyloxymethyl, or the like to form an ester; or the hydroxy group of the carboxy or sulfo group may be substituted by amino, mono- or dimethylamino, mono- or diethylamino, mono- or dipropylamino, mono- or diisopropylamino, or the like to form an amide.

The representative examples of the aliphatic hydrocarbon group having an appropriate substituent or substituents at optional positions may be an alkoxyalkyl (e.g. methoxymethyl), an alkylthioalkyl (e.g. methylthioethyl), an alkanoylaminoalkyl (e.g. acetylaminoethyl), an alkanoylthioalkyl (e.g. acetylthiomethyl), a nitroalkyl (e.g. nitroethyl), a cyanoalkyl (e.g. cyanomethyl), a haloalkyl (e.g. chloromethyl or trichloromethyl), an oxo substituted bicycloalkyl (e.g. 1,7,7-trimethyl-2-oxobicyclo[2,2,1]-heptane-3-yl), an oxo substituted bicycloalkylalkyl (e.g. (7,7-dimethyl-2-oxobicyclo[2,2,1]heptan-1-yl)methyl), an alkoxycarbonylalkyl (e.g. methoxycarbonylethyl), a benzloxycarbonylamino and alkoxycarbonyl substituted alkyl (e.g. (2-benzyloxycarbonylamino-2-ethoxycarbonyl)ethyl), a sulfoalkyl (e.g. sulfomethyl), a halosulfonylalkyl (e.g. chlorosulfonylmethyl or chlorosulfonylethyl), an alkanoyloxyalkyl (e.g. acetoxyethyl), an alkanoyloxyaminoalkyl (e.g. acetoxyaminoethyl), a dialkylaminoalkyl (e.g. dimethylaminoethyl), an aralkyl (e.g. benzyl), a phenylalkenyl (e.g. styryl), a nitro substituted aralkyl (e.g. 4-nitrobenzyl), an alkanoylalkyl (e.g. acetylmethyl), a piperidylalkyl (e.g. 2-piperidylpropyl), a morpholinoalkyl (e.g. 3-morpholinopropyl), or the like.

The substituted or unsubstituted aryl group being one of the organic group for $R_1$ includes the same aryl group as mentioned as the one of the substituents of the aliphatic hydrocarbon group, and the substituents of the aryl group include an alkyl (e.g. methyl, ethyl or propyl), an alkenyl (e.g. vinyl, 1-propenyl or 2-propenyl), an alkynyl (e.g. ethynyl or 2-propynyl), a cycloalkyl (e.g. cyclopropyl, cyclobutyl, cyclopentyl or cyclohexyl), carbamoyl, a mono- or dialkylcarbamoyl (e.g. methylcarbamoyl, ethylcarbamoyl, methylethylcarbamoyl, dimethylcarbamoyl or diethylcarbamoyl) as well as the substituents as mentioned as these of the above aliphatic hydrocarbon group. The representative examples of the aryl having an appropriate substituent or substituents may be a halogen substituted aryl (e.g. chlorophenyl or bromophenyl), a nitro substituted aryl (e.g. nitrophenyl), an alkenyl substituted aryl (e.g. vinylphenyl), an alkoxycarbonyl substituted aryl (e.g. methoxycarbonylphenyl or ethoxycarbonylphenyl), a hydroxy substituted aryl (e.g. hydroxyphenyl or hydroxynaphthyl), or the like. When the substituents of the aryl group are amino, hydroxy, mercapto, carboxy and sulfo, or when the aryl group, acyl group or heterocyclic group being one of the substituents of the aryl group contains amino, hydroxy, mercapto, carboxy or sulfo substituent, these substituents may be protected by an appropriate protecting group as mentioned above for the aliphatic hydrocarbon group.

The substituted or unsubstituted heterocyclic group being one of the organic group for $R_1$ includes the same aliphatic or aromatic mono- or polycyclic heterocyclic group containing at least one hetero atom selected from oxygen, sulfur, nitrogen, or the like as mentioned as the one of the substituents of the aliphatic hydrocarbon group, and the substituents of the heterocyclic group includes an alkyl (e.g. methyl, ethyl or propyl), an alkenyl (e.g. vinyl, 1-propenyl or 2-propenyl), an alkynyl (e.g. ethynul or 2-propynyl), a cycloalkyl (e.g. cyclopropyl, cyclobutyl, cyclopentyl or cyclohexyl), or the like as well as the substituents as mentioned as those of the above aliphatic hydrocarbon group. When the substituents of the heterocyclic group are amino, hydroxy, mercapto, carboxy and sulfo, or when the aryl group, acyl group or heterocyclic group being one of the substituents of the heterocyclic group contains amino, hydroxy, mercapto, carboxy or sulfo substituent, these substituents may be protected by an appropriate protecting group as mentioned above for the aliphatic hydrocarbon group.

The residue of a strongly acidic N-hydroxy compound for $R_2O-$ in the formula (I) includes a residue of a strongly acidic aliphatic or aromatic N-hydroxy compound, for instance a group of the formula:

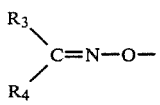

wherein $R_3$ and $R_4$ are the same or different and are each an electron attractive group, and a group of the formula:

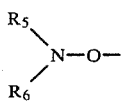

wherein $R_5$ and $R_6$ are the same or different and are each hydrogen, acyl, aryl or arylazo group, and a residue of a nitrogen-containing heterocyclic N-hydroxy compound.

The examples of the electron attractive group for $R_3$ and $R_4$ may be nitro, cyano, carbamoyl, an esterified carboxy group, such as an alkoxycarbonyl (e.g. methoxycarbonyl, ethoxycarbonyl, propoxycarbonyl, isopropoxycarbonyl, butoxycarbonyl or isobutoxycarbonyl), an aralkyloxycarbonyl (e.g. benzyloxycarbonyl or phenethyloxycarbony), or an aryloxycarbonyl (e.g. phenoxycarbonyl or xylyloxycarbonyl), or the like.

The examples of the aryl group for $R_5$ and $R_6$ may be phenyl, naphthyl, or the like, the arylazo group may be phenylazo, naphthylazo, or the like, and further the acyl group may be the same acyl group as mentioned above as the substituent of the aliphatic hydrocarbon group for $R_1$.

The nitrogen-containing heterocyclic group in the residue of a nitrogen-containing heterocyclic N-hydroxy compound includes aliphatic or aromatic mono- or polycyclic heterocyclic groups containing at least one nitrogen atom and optionally one or more other hetero atoms such as oxygen or sulfur. The examples of the heterocyclic groups may be an unsaturated 3 to 8-membered heteromonocyclic containing 1 to 4 nitrogen atom(s) (e.g. pyrrolyl, dihydropyridyl, imidazolyl, imidazolinyl, triazolyl or tetrazolyl), a saturated 3 to 8-membered heteromonocyclic containing 1 to 2 nitrogen atom(s) (e.g. pyrrolidinyl, piperidino, homopiperidino or piperazinyl), an unsaturated condensed-heterocyclic containing 1 to 3 nitrogen atom(s) (e.g. indolyl, indolinyl, isoindolinyl, dihydroquinolyl, dihydroisoquinolyl, dihydroquinazolinyl, benzotriazolyl, dihydrobenzotriazinyl, benzimidazolyl or benzimidazolinyl), an unsaturated 3 to 8-membered heteromonocyclic containing an oxygen atom and 1 to 3 nitrogen atom(s) (e.g. oxazolinyl, oxadiazolinyl or oxatriazolinyl), a saturated 3 to 8-membered heteromonocyclic containing an oxygen atom and 1 to 3 nitrogen atom(s) (e.g. morpholino), an unsaturated condensed-heterocyclic containing an oxygen atom and 1 to 2 nitrogen atom(s) (e.g. benzoxazolinyl), an unsaturated 3 to 8-membered heteromonocyclic containing a sulfur atom and 1 to 3 nitrogen atom(s) (e.g. thiazolinyl, thiadiazolinyl or thiatriazolinyl), an unsaturated condensed-heterocyclic containing a sulfur atom and 1 to 4 nitrogen atom(s) (e.g. benzothiazolinyl or thiazolotriazolyl), or the like. The heterocyclic groups may have one or more substituents at optional positions. The examples of the substituents may be an alkoxy, an alkylthio, amino, mercapto, nitro, cyano, a halogen, oxo, carboxy, sulfo, a halosulfonyl, hydroxy, hydroxyamino, a mono- or dialkylamino, an aryl, an acyl and a heterocyclic group as mentioned as the substituents of the above aliphatic hydrocarbon groups for $R_1$, and further may be an alkyl (e.g. methyl, ethyl, propyl or butyl), an alkenyl (e.g. vinyl, 1-propenyl or 2-propenyl), a mono or dialkylaminoalkyl (e.g. mono- or dimethylaminomethyl, mono-or diethylaminomethyl, mono- or dimethylaminoethyl, or mono- or diethylaminoethyl), a haloalkyl (e.g. chloromethyl, bromomethyl, chloroethyl, dichloromethyl, trichloromethyl, tribromomethyl, trifluoromethyl or trichloroethyl), or the like. When the substituents of the heterocyclic groups are amino, hydroxy, mercapto, carboxy and sulfo, these substituents may be protected by a protecting group as mentioned above.

The examples of the heterocyclic group having an appropriate substituent or substituents may be an oxo substituted pyrrolidinyl (e.g. 2,5-dioxopyrrolidin-1-yl or 2-oxopyrrolidin-1-yl), an oxo substituted piperidino (e.g. 2,6-dioxopiperidino), an oxo substituted dihydropyridyl (e.g. 2-oxo-1,2-dihydropyridin-1-yl), a halogen, alkyl and oxo substituted dihydropyridyl (e.g. 3,5-dichloro-4,6-dimethyl-2-oxo-1,2-dihydropyridin-1-yl), an oxo, phenyl and alkyl substituted imidazolinyl (e.g. 2-oxo-4-phenyl-5-methylimidazolin-1-yl), a phenyl substituted triazolyl (e.g. 4,5-diphenyl-1,2,3-triazol-1-yl), an oxo substituted dihydroquinazolinyl (e.g. 4-oxo-3,4-dihydroquinazolin-3-yl), an oxo and phenyl substituted dihydroquinazolinyl (e.g. 4-oxo-2-pheny-3,4-dihydroquinazolin-3-yl), a benzoyl, cyano and/or alkyl substituted benzimidazolyl (e.g. 2-benzoylbenzimidazol-1-yl, 2-cyanobenzimidazol-1-yl or 2-benzoyl-6-methylbenzimidazol-1-yl), an oxo and phenyl substituted benzimidazolinyl (e.g. 2-oxo-3-phenylbenzimidazolin-1-yl), an oxo and halogen substituted indolinyl (e.g. 2-oxo-6-chloroindolin-1-yl), an oxo substituted isoindolinyl (e.g. 1,3-dioxoisoindolin-2-yl), a nitro, dialkylamino, halogen, alkenyl, dialkylaminoalkyl, alkyl, haloalkyl, cyano and/or alkoxy substituted benzotriazolyl (e.g. 6-nitro-1,2,3-benzotriazol-1-yl, 6-dimethylamino-1,2,3-benzotriazol-1-yl, 4-chloro-1,2,3-benzotriazol-1-yl, 6-chloro-1,2,3-benzotriazol-1-yl, 6-vinyl-1,2,3-benzotriazol-1-yl, 6-dimethylaminomethyl-1,2,3-benzotriazol-1-yl, 5-methyl-1,2,3-benzotriazol-1-yl, 7-chloromethyl-1,2,3-benzotriazol-1-yl, 6-methyl-5-cyano-1,2,3-benzotriazol-1-yl, 5-chloro-6-nitro-1,2,3-benzotriazol-1-yl, 6-methoxy-1,2,3-benzotriazol-1-yl, or 4,5,6,7-tetrachloro-1,2,3-benzotriazol-1-yl), an oxo and/or halogen substituted dihydrobenzotriazinyl (e.g. 4-oxo-3,4-dihydro-1,2,3-benzotriazin-3-yl or 6-bromo-4-oxo-3,4-dihydro-1,2,3-benzotriazin-3-yl), or the like.

The strongly acidic N-hydroxy compound containing the group: $R_2O—$, which can be shown by the formula: $R_2OH$, has preferably a high acidity, for instance has preferably a pKa value of not more than 6.

The representative examples of fthe present sulfonic acid ester (I) may be an alkyl 2-alkanesulfonyloxyimino-2-cyanoacetate (e.g. ethyl 2-methanesulfonyloxyimino-2-cyanoacetate), a 2-alkanesulfonyloxyimino-2-cyanoacetamide (e.g. 2-methanesulfonyloxyimino-2-cyanoacetamide), a N-alkanesulfonyloxysuccinimide (e.g. N-methanesulfonyloxysuccinimide), a 1-alkanesulfonyloxybenzotriazole (e.g. 1-methanesulfonyloxy-1,2,3-benzotriazole or 1-n-butanesulfonyloxy-1,2,3-benzotriazole), a nitro substituted 1-alkanesulfonyloxybenzotriazole (e.g. 1-methanesulfonyloxy-6-nitro-1,2,3-benzotriazole), a 1-(oxo substituted bicycloalkylalkylsulfonyloxy)benzotriazole (e.g. 1-(DL-10-camphor-sulfonyloxy)-1,2,3-benzotriazole), a halogen or nitro substituted 1-(oxo substituted bicycloalkylalkylsulfonyloxy)benzotriazole (e.g. 1-(DL-10-camphor-sulfonyloxy)-6-chloro-1,2,3-benzotriazole or 1-(DL-10-camphor-sulfonyloxy)-6-nitro-1,2,3-benzotriazole), an aralkylsulfonyloxybenzotriazole (e.g. 1-benzylsulfonyloxy-1,2,3-benzotriazole), a halogen substituted aralkylsulfonyloxybenzotriazole (e.g. 1-benzylsulfonyloxy-6-chloro-1,2,3-benzotriazole), an arylalkenesulfonyloxybenzotriazole (e.g. 1-(β-styrenesulfonyloxy)-1,2,3-benzotriazole), a halogen or alkenyl substituted 1-alkanesulfonyloxybenzotriazole (e.g. 1-methanesulfonyloxy-4-chloro-1,2,3-benzotriazole, 1-methanesulfonyloxy-6-chloro-1,2,3-benzotriazole, 1-n-butanesulfonyloxy-6-chloro-1,2,3-benzotriazole or 1-methanesulfonyloxy-6-vinyl-1,2,3-benzotriazole), an alkyl 2-arylsulfonyloxyimino-2-cyanoacetate (e.g. ethyl 2-(p-toluenesulfonyloxyimino)-2-cyanoacetate), a 1-arylsulfonyloxybenzotriazole (e.g. 1-benzenesulfonyloxy-1,2,3-benzotriazole, 1-(p-toluenesulfonyloxy)-1,2,3-benzotriazole or 1-mesitylenesulfonyloxy- 1,2,3-benzotriazole), a nitro, halogen or alkenyl substituted 1-arylsulfonyloxybenzotriazole (e.g. 1-benzenesulfonyloxy-6-nitro-1,2,3-benzotriazole, 1-benzenesulfonyloxy-6-chloro-1,2,3-benzotriazole, 1-(p-toluenesulfonyloxy)-6-nitro-1,2,3-benzotriazole, 1-(p-toluenesulfonyloxy)-6-chloro-1,2,3-benzotriazole or 1-(p-toluenesulfonyloxy)-6-vinyl-1,2,3-benzotriazole), an alkenyl substituted 1-(alkenyl substituted arylsulfonyloxy)benzotriazole (e.g. 1-(p-vinylbenzenesulfonyloxy)-6-vinyl-1,2,3-benzotriazole), a 1-(halogen substituted arylsulfonyloxy)benzotriazole (e.g. 1-(p-chlorobenzenesulfonyloxy)-1,2,3-benzotriazole), a halogen or alkenyl substituted 1-(halogen substituted arylsulfonyloxy)benzotriazole (e.g. 1-(p-chlorobenzenesulfonyloxy)-6-chloro-1,2,3-benzotriazole or 1-(p-chlorobenzenesulfonyloxy)-6-vinyl-1,2,3-benzotriazole), a 1-(nitro substituted arylsulfonyloxy)benzotriazole (e.g. 1-(p-nitrobenzenesulfonyloxy)-1,2,3-benzotriazole), a 1-(pyridylsulfonyloxy)benzotriazole (e.g. 1-(3-pyridylsulfonyloxy)-1,2,3-benzotriazole), an oxo substituted 3-alkane(or aryl)sulfonyloxy-dihydrobenzotriazine (e.g. 4-oxo-3,4-dihydro-3-methanesulfonyloxy-1,2,3-benzotriazine or 4-oxo-3,4-dihydro-3-benzenesulfonyloxy-1,2,3-benzotriazine), an oxo and phenyl substituted 1-alkanesulfonyloxybenzimidazoline (e.g. 1-methanesulfonyloxy-2-oxo-3-phenylbenzimidazoline or 1-n-butanesulfonyloxy-2-oxo-3-phenylbenzimidazoline), an oxo and phenyl substituted 1-(halogen substituted arylsulfonyloxy)benzimidazoline (e.g. 1-(p-chlorobenzenesulfonyloxy)-2-oxo-3-phenylbenzimidazoline), a 1-alkenesulfonyloxybenzotriazole (e.g. 1-vinylsulfonyloxy-1,2,3-benzotriazole), an alkenyl or halogen substituted 1-alkenesulfonyloxybenzotriazole (e.g. 1-vinylsulfonyloxy-6-vinyl-1,2,3-benzotriazole or 1-vinylsulfonyloxy-6-chloro-1,2,3-benzotriazole), or the like.

The sulfonic acid esters of the formula (I) may be prepared in the same manner as described hereinafter for the preparation of the sulfonic acid esters (II).

The sulfonic acid esters of the formula (I) are most novel compounds but include a few old compounds.

The present invention provides also a novel sulfonic acid ester and a process for the preparation thereof.

The novel sulfonic acid ester of the present invention has the following formula:

wherein $R_1'$ is a member selected from the group consisting of an alkyl having 1 to 6 carbon atoms, an oxo substitute bicycloalkylalkyl having 7 to 10 carbon atoms in the bicycloalkyl moiety and having 1 to 6 carbon atoms in the alkyl moiety, a phenylalkyl having 1 to 6 carbon atoms in the alkyl moiety, a phenylalkenyl having 2 to 6 carbon aoms in the alkenyl moiety, phenyl, a phenyl having 1 to 3 substituent(s) selected from the group consisting of an alkyl having 1 to 6 carbon atoms, an alkenyl having 2 to 6 carbon atoms, a halogen and nitro, and pyridyl, and $R_2'O-$ is a member selected from the group consisting of benzotriazolyloxy, benzotriazolyloxy having one substituent selected from the group consisting of nitro, a halogen and an alkenyl having 2 to 6 carbon atoms, and an oxo substituted dihydrobenzotriazinyloxy, with proviso that when $R_1'$ a phenyl having one alkyl, $R_2'O-$ is not benzotriazolyloxy.

The alkyl group, the oxo substituted bicycloalkylalkyl, the alkyl or alkenyl moiety in the phenyl-alkyl or phenyl-alkenyl and the alkyl, alkenyl or halogen which is the substituent of phenyl for $R_1'$ are the same as defined above for $R_1$ in the sulfonic acid esters (I). And the halogen or alkenyl which is the substituent of benzotriazolyloxy and oxo substituted dihydrobenzotriazinyloxy for $R_2'O-$ are the same as defined for $R_2O-$ in the sulfonic acid esters (I).

The representative examples of such sulfonic acid ester may be 1-methanesulfonyloxy-1,2,3-benzotriazole, 1-methanesulfonyloxy-6-nitro-1,2,3-benzotriazole, 1-(3-pyridylsulfonyloxy)-1,2,3-benzotriazole, 1-(DL-10-camphor-sulfonyloxy)-6-nitro-1,2,3-benzotirazole, 1-methanesulfonyloxy-4-chloro-1,2,3-benzotriazole, 1-methanesulfonyloxy-6-chloro-1,2,3-benzotriazole, 1-(DL-10-camphorsulfonyloxy)-6-chloro-1,2,3-benzotriazole, 1-benzylsulfonyloxy-1,2,3-benzotriazole, 1-(β-styrenesulfonyloxy)-1,2,3-benzotriazole, 1-(DL-10-camphor-sulfonyloxy)-1,2,3-benzotriazole, 1-(n-butanesulfonyloxy)-1,2,3-benzotriazole, 1-(n-butanesulfonyloxy)-6-chloro-1,2,3-benzotriazole, 1-benzylsulfonyloxy-6-chloro-1,2,3-benzotriazole, 1-methanesulfonyloxy-6-vinyl-1,2,3-benzotriazole, 4-oxo-3,4-dihydro-3-methanesulfonyloxy-1,2,3-benzotriazine, 1-benzenesulfonyloxy-6-nitro-1,2,3-benzotriazole, 1-(p-toluenesulfonyloxy)-6-nitro-1,2,3-benzotriazole, 1-benzenesulfonyloxy-6-chloro-1,2,3-benzotriazole, 1-(p-chlorobenzenesulfonyloxy)-6-chloro-1,2,3-benzotriazole, 1-(p-vinylbenzenesulfonyloxy)-6-vinyl-1,2,3-benzotriazole, 1-(p-chlorobenzenesulfonyloxy)-6-vinyl-1,2,3-benzotriazole, 1-(p-toluenesulfonyloxy)-6-vinyl-1,2,3-benzotriazole, 1-(p-toluenesulfonyloxy)-6-chloro-1,2,3-benzotriazole, 4-oxo-3,4-dihydro-3-benzenesulfonyloxy-1,2,3-benzotriazine, 1-(p-nitrobenzenesulfonyloxy)-1,2,3-benzotriazole, 1-(p-chlorobenzenesulfonyloxy)-1,2,3-benzotriazole, 1-benzenesulfonyloxy-1,2,3-benzotriazole, 1-(2,4,6-trimethylbenzenesulfonyloxy-1,2,3-benzotriazole, or the like.

The sulfonic acid esters of the formula (II) may be prepared by reacting a sulfonic acid of the formula:

$$R_1'-SO_3H \qquad (III)$$

wherein $R_1'$ is as defined above, or its reactive derivative at the sulfo group with a N-hydroxy compound of the formula:

$$R_2'OH \qquad (IV)$$

wherein R$_2$'O— is as defined above, or its salt.

The reactive derivative of the sulfonic acid (III) may be an acid anhydride, such as dialkylphosphoric acid mixed anhydride, phenylphosphoric acid mixed anhydride, diphenylphosphoric acid mixed anhydride, dibenzylphosphoric acid mixed anhydride, halogenated phosphoric acid mixed anhydride, dialkylphosphorous acid mixed anhydride, sulfurous acid mixed anhydride, thiosulfuric acid mixed anhydride, hydrohalogenic acid mixed anhydride (e.g. acid chloride), sulfuric acid mixed anhydride, symmetrical acid anhydride, or the like.

The salt of the N-hydroxy compound (IV) may be a salt of an alkali metal (e.g. sodium or potassium), an alkaline earth metal (e.g. calcium or magnesium), a tertiary organic base (e.g. trimethylamine, triethylamine, triethanolamine, N,N-dimethylaniline, N,N-dimethylbenzylamine or pyridine), or the like.

The reaction may be carried out by treating the sulfonic acid (III) or its reactive derivative with an equimolar amount of N-hydroxy compound (IV) or its salt.

The reaction may usually be carried out in an appropriate solvent. The examples of the solvent may preferably be benzene, ethyl acetate, dioxane, water, or the like, but may be any other solvent such as chloroform, ether, dichloromethane, or the like which does not give any undesirable effect to the reaction. These solvent may be used alone or in a mixture thereof. The reaction may be usually carried out in the presence of an inorganic base, such as an alkali metal hydroxide (e.g. sodium hydroxide or potassium hydroxide), an alkaline earth metal hydroxide (e.g. calcium hydroxide or magnesium hydroxide), an alkali metal carbonate (e.g. sodium carbonate or potassium carbonate), an alkaline earth metal carbonate (e.g. calcium carbonate or magnesium carbonate), an alkali metal hydrogen carbonate (e.g. sodium hydrogen carbonate or potassium hydrogen carbonate), or the like; or an organic base, such as trimethylamine, triethylamine, triethanolamine, N,N-dimethylaniline, N,N-dimethylbenzylamine, N,N'-dimethylpiperazine, pyridine, quinoline, or the like: or a mixture thereof.

When a free sulfonic acid (III) is used, it is preferable to use an appropriate condensation agent. The examples of the condensation agent may be N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, or the like.

The reaction temperature is not limited to a specific temperature, but the reaction may be usually carried out under ice-cooling or at room temperature.

When the amino, hydroxy, mercapto, carboxy or sulfo group of the starting materials is protected by an appropriate protecting group, the protecting group may be removed on the way or after the reaction, on the other hand, the free amino, hydroxy, mercapto, carboxy or sulfo group may be protected by an appropriate protecting group on the way or after the reaction.

The product thus prepared is isolated by a conventional method from the reaction mixture.

The amidation of the present invention may be carried out by reacting a compound having a carboxy group with a compound having an amino or imino group which can be acylated in the presence of a sulfonic acid ester of the formula (I).

The compound having a carboxy group includes every kinds of compounds having at least one carboxy group in the molecule, and may be saturated or unsaturated, straight, branched or cyclic, substituted or unsubstituted aliphatic, aromatic or heterocyclic compounds.

The compound having an amino or imino group which can be acylated includes every kids of ammonia, primary or secondary amines which contains a saturated or unsaturated, straight, branched or cyclic, substituted or unsubstituted aliphatic, aromatic or heterocyclic group within the molecule. In case of heterocyclic compound, the imino group may be contained as a ring-forming hetero atom.

The carboxy group and the amino or imino group which can be acylated may be included in different molecules, but the both group may be included in a single molecule. When the both groups are included in a single molecule, both groups may be reacted with each other within the molecule by intramolecular reaction to form an amido bond. In such case, at least two carbon atoms may preferably intervene between the carboxy group and the amino or imino groups.

The sulfonic acid esters (I) may be added in any order to the reaction system. For instance, the sulfonic acid esters (I) may be added to a compound having a carboxy group and thereto may be added a compound having an amino or imino group; the sulfonic acid esters (I) may be added to a compound having an amino or imino group and thereto may be added a compound having a carboxy group; or the three components may be simultaneously mixed. When a compound having a carboxy group is reacted with a compound having both carboxy group and amino or imino group within a single molecule, it is preferable that the sulfonic acid esters (I) is first added to the compound having a carboxy group and then is added thereto the compound having both carboxy and amino or imino groups.

The amidation reaction may be usually carried out in an appropriate solvent. The examples of the solvent may preferably be ethyl acetate, chloroform, dimethylformamide, dichloromethane, tetrahydrofuran, acetone, water, or the like, but there may be used any other solvent which does not give any undesirable effect to the reaction. These solvents may be used alone or in a mixture thereof. The reaction may be optionally carried out in the presence of an inorganic base, such as an alkali metal hydroxide (e.g. sodium hydroxide or potassium hydroxide), an alkaline earth metal hydroxide (e.g. calcium hydroxide or magnesium hydroxide), an alkali metal carbonate (e.g. sodium carbonate or potassium carbonate), an alkaline earth metal carbonate (e.g. calcium carbonate or magnesium carbonate), an alkali metal hydrogen carbonate (e.g. sodium hydrogen carbonate or potassium hydrogen carbonate), or the like; or an organic base, such as an alkali metal acetate (e.g. sodium acetate or potassium acetate), trimethylamine, triethylamine, triethanolamine, N,N-dimethylaniline, N,N-dimethylbenzylamine, N,N'-dimethylpiperazine, N-methylmorpholine, pyridine, quinoline, or the like; or a mixture thereof.

The reaction temperature is not limited to a specific temperature, but the reaction may be usually carried out under ice-cooling or at room temperature.

The product thus prepared may be isolated by a conventional method.

The esterification of the present invention may be carried out by reacting a compound having a carboxy group with a compound having a hydroxy group in the presence of a sulfonic acid ester of the formula (I).

The compound having a carboxy group may be the same as mentioned in the above amidation.

The compound having a hydroxy group includes every kinds of compounds having at least one hydroxy group in the molecule, and may be saturated or unsaturated, straight, branched or cyclic, substituted or unsubstituted aliphatic, aromatic or heterocyclic compounds.

The sulfonic acid esters (I) may be added in any order to the reaction system. For instance, the sulfonic acid esters (I) may be added to a compound having a carboxy group and thereto may be added a compound having a hydroxy group, or the sulfonic acid esters (I) may be added to a mixture of a compound having a carboxy group and a compound having a hydroxy group. When the sulfonic acid esters (I) is firstly reacted with a compound having a carboxy group, an intermediate of the formula:

$$R'-OR_2 \qquad (V)$$

wherein R' is an acyl which is derived from the compound having a carboxy group by removing hydroxy group therefrom, and $R_2O-$ is as defined above, may be occasionally produced. After isolating or without isolation, the intermediate (V) may be then reacted with a compound having a hydroxy group to give the desired ester compound.

The esterification reaction may be usually carried out in an appropriate solvent. The examples of the solvent may preferably be ethyl acetate, chloroform, benzene, ether, dichloromethane, tetrahydrofuran, acetonitrile, or the like, but there may be used any other solvent which does not give any undesirable effect to the reaction and does not have hydroxy group. These solvents may be used alone or in a mixture thereof. The reaction may be optionally carried out in the presence of an organic base, such as trimethylamine, triethylamine, triethanolamine, N,N-dimethylaniline, N,N-dimethylbenzylamine, N,N'-dimethylpiperazine, N-methyl-morpholine, pyridine, quinolie, or the like, or a mixture thereof.

The reaction temperature is not particularly limited, but the reaction may be usually carried out under ice-cooling or at room temperature. When the intermediate (V) prepared by the reaction of the sulfonic acid esters (I) with a compound having a carboxy group is reacted with a compound having a hydroxy group, the reaction may be carried out at room temperature or under cooling in the presence of a base, or may be carried out at a temperature of the boiling point of the solvent in case of using no base.

The product thus produced may be isolated by a conventional method.

The terms "alkyl", "alkenyl", "alkynyl", "alkoxy" and "alkanoyl" where used herein denote the groups having 1 to 6 carbon atoms, the terms "cycloalkyl" and "cycloalkenyl" denote the groups having 3 to 6 carbon atoms, the term "bicycloalkyl" denotes the group having 7 to 10 carbon atoms and the terms "aralkyl", "aralkanoyl", "alkanesulfonyl" and "alkenesulfonyl" denote the groups having 1 to 6 carbon atoms in the alkyl, alkanoyl, alkane or alkene moiety.

The amidation of the present invention is illustrated by the following Examples.

EXAMPLE 1

Acetic acid (0.3 g) and triethylamine (0.7 ml) are dissolved in ethyl acetate (10 ml), and thereto is added ethyl 2-methanesulfonyloxyimino-2-cyanoacetate (1.1 g) and the mixture is stirred for 40 minutes. To the solution is added aniline (0.5 g) and the mixture is stirred for 2 hours. The reaction mixture is washed well with 1 N aqueous sodium hydrogen carbonate, water and 1 N hydrochloric acid in order and then dried over anhydrous magnesium sulfate. After drying, the solvent is distilled off to give flasks of acetanilide (0.6 g), melting poit: 95°–105° C. The product recrystallized from water has a melting point of 104°–108° C.

EXAMPLE 2

Acetic acid (0.3 g), triethylamine (0.7 ml) and aniline (0.5 g) are dissolved in ethyl acetate (10 ml), and thereto is added 1-methanesulfonyloxy-1,2,3-benzotriazole (1.05 g), and the mixture is stirred at room temperature for 1 hour. After allowing to stand overnight, the reaction mixture is extracted with ethyl acetate. The extract is washed with water and dried over anhydrous magnesium sulfate. After drying, the solvent is distilled off to give acetanilide (0.7 g). The product recrystallized from water has a melting point of 110°–112° C.

EXAMPLE 3

1 H-Tetrazol-1-acetic acid (1.28 g) and triethylamine (1.4 ml) are dissolved in a mixture of ethyl acetate (10 ml) and chloroform (5 ml), and thereto is added ethyl 2-methanesulfonyloxyimino-2-cyanoacetate (2.2 g). The mixture is stirred at room temperature for 2 hours and thereto is added aniline (0.95 g), and the mixture is further stirred for 2 hours. To the solution is added water, and the mixture is allowed to stand overnight. The crystals thus precipitated are separated by filtration and recrystallized from chlorofor to give 2-(1 H-tetrazol-1-yl)acetanilide (0.3 g), melting point: 192°–193° C. (decomp). From the mother liquid 2-(1 H-tetrazol-1-yl)acetanilide (0.4 g) having a melting point of 190°–191° C. (decomp) is further obtained.

Anal. Calcd. for $C_9H_9ON_5$: C,53.19; H,4.46; N,34.47. Found: C,52.92; H,4.26; N,34.07.

EXAMPLE 4

1 H-Tetrazol-1-acetic acid (1.28 g), triethylamine (1.4 ml) and aniline (0.95 g) are dissolved in ethyl acetate (10 ml), and thereto is added ethyl 2-methanesulfonyoxyimino-2-cyanoacetate (2.2 g) at room temperature and the mixture is stirred at room temperature for 2.5 hours. To the solution is added water and the mixture is allowed to stand overnight. The crystals thus precipitated are separated by filtration and recrystallized from chloroform to give 2-(1 H-tetrazol-1-yl)acetanilide (1.75 g), melting point: 192°–193° C. (decomp).

EXAMPLE 5

N-Benzyloxycarboyl-L-proline (1.25 g) and L-leucine ethyl ester hydrochloride (1.0 g) are suspended into chloroform (10 ml), and therein is dissolved N-methylmorpholine (1.10 ml). To the solution is added ethyl 2-methanesulfonyloxyimino-2-cyanoacetate (1.1 g) and the mixture is stirred at room temperature for 16 hours. After reaction, the reaction mixture is extracted with ethyl acetate. The extract is washed with water, 1 N aqueous sodium hydrogen carbonate, water, 1 N hydrochloric acid and water in order and then dried over anhydrous magnesium sulfate. After drying, the solvent is distilled off and the resulting residue is crystallized from petroleum ether to give N-(N-benzyloxycarbonyl-L-prolyl)-L-leucine ethyl ester (1.4 g), melting point:65°–67° C.

Anal. Calcd. for $C_{21}H_{30}O_5N_2$: C,64.59; H,7.74; N,7.18. Found: C,64.68; H,7.88; N,7.20.

EXAMPLE 6

N-Benzyloxycarbonyl-L-proline (1.25 g) and L-leucine ethyl ester hydrochloride (1.0 g) are suspended into chloroform (10 ml), and therein is dissolved triethylamine (1.40 ml). To the solution is added ethyl 2-methanesulfonyloxyimino-2-cyanoacetate (1.1 g) and the mixture is stirred at room temperature for 16 hours. After reaction, the reaction mixture is extracted with ethyl acetate. The extract is washed with water, 1 N aqueous sodium hydrogen carbonate, water, 1 N hydrochloric acid and water in order and then dried over anhydrous magnesium sulfate. After drying, the solvent is distilled off and the resulting residue is crystallized from petroleum ether to give N-(N-benzyloxycarbonyl-L-prolyl)-L-leucine ethyl ester (0.8 g), melting point: 65°–67° C.

EXAMPLE 7

N-Benzoyloxycarbonyl-L-proline (1.25 g) and L-leucine ethyl ester hydrochloride (1.0 g) are suspended into chloroform (10 ml), and therein is dissolved triethylamine (1.40 ml). To the solution is added 1-methanesulfonyloxy-1,2,3-benzotriazole (1.07 g) and the mixture is stirred at room temperature for 16 hours. After reaction, the reaction mixture is extracted with ethyl acetate. The extract is washed with water, 1 N aqueous sodium hydrogen carbonate, water, 1 N hydrochloric acid and water in order and then dried over anhydrous magnesium sulfate. After drying, the solvent is distilled off and the resulting residue is crystallized from petroleum ether to give N-(N-benzlyloxycarbonyl-L-prolyl)-L-leucine ethyl ester (1.45 g), melting point: 65°–66° C.

EXAMPLE 8

N-Benzyloxycarbonyl-L-proline (1.25 g) and L-leucine ethyl ester hydrochloride (1.0 g) are suspended into chloroform (10 ml), and therein is dissolved triethylamine (1.4 ml). To the solution is added ethyl 2-(p-toluenesulfonyloxyimino)-2-cyanoacetate (1.5 g) and the mixture is stirred at room temperature for 16 hours. After reaction, the reaction mixture is extracted with ethyl acetate. The exatract is washed with water, 1 N aqueous sodium hydrogen carbonate, water, 1 N hydrochloric acid and water in order and then dried over anhydrous magnesium sulfate. After drying, the solvent is distilled off and the residual oily substance (1.6 g) is dissolved in chloroform and then the mixture is subjected to a silica gel column chromatography (developer: chloroform). The first fraction thus obtained is concentrated and the resulting residue is crystallized from ether-petroleum ether to give N-(N-benzyloxycarbonyl-L-prolyl)-L-leucine ethyl ester (80 mg), melting point: 60°–64° C. The product is identified with an authentic sample by infrared spectrum.

EXAMPLE 9

N-Benzyloxycarbonyl-S-benzyl-L-cysteine (1.73 g) and glycine ethyl ester hydrochloride (0.70 g) are dissolved in dimethylformamide (12 ml), and thereto are added triethylamine (1.40 ml) and further ethyl 2-methanesulfonyloxyimino-2-cyanoacetate (1.1 g). The mixture is allowed to stand at room temperature for 14 hours. To the reaction mixture are added water and ethyl acetate, and the ethyl acetate layer is separated, washed with water, 1 N hydrochloric acid, a saturated aqueous sodium hydrogen carbonate and water in order and then dried over anhydrous magnesium sulfate. After drying, the solvent is distilled off and the resulting residue is crystallized from ethanol-petroleum ether, separated by filtration and dried to give N-(N-benzyloxycarbonyl-S-benzyl-L-cysteinyl)glycine ethyl ester (0.5 g), melting point: 93°–95° C. The product is identified with an authentic sample by infrared spectrum.

EXAMPLE 10

N-Benzyloxycarbonyl-S-benzyl-L-cysteine (1.73 g) and glycine ethyl ester hydrochloride (0.70 g) are suspended into chloroform (20 ml) and therein is dissolved triethylamine (1.4 ml). To the solution is added 1-methanesulfonyloxy-1,2,3-benzotriazole (1.07 g) with stirring under ice-cooling. The mixture is stirred for 2 hours and then allowed to stand overnight. To the reaction mixture are added water and ethyl acetate. The ethyl acetate layer is separated and washed with water, 1 N hydrochloric acid, a saturated aqueous sodium hydrogen carbonate and water in order and then dried over anhydrous magnesium sulfate. After drying, the solvent is distilled off and the resulting residue is crystallized from petroleum ether to give N-(N-benzyloxycarbonyl-S-benzyl-L-cysteinyl)glycine ethyl ester (1.25 g), melting pont: 89°–93° C. The product is identified with an authentic sample by infrared spectrum.

EXAMPLE 11

2-Methoxy-4-amino-5-chlorobenzoic acid (1.0 g) and 1-methanesulfoyloxy-1,2,3-benzotriazole (1.07 g) are suspended into chloroform (15 ml) and therto is added dropwise triethylamine (0.7 ml) with stirring under ice-cooling to give a clear solution. To the solution is added 2-(diethylamino)ethylamine (0.6 g) at room temperature and the mixture is allowed to stand for 18 hours. The solvent is then distilled off and thereto are added water and 1 N aqueous sodium hydroxide. The resulting crystals are separated by filtration, washed with water and then dried to give N-(2-diethylaminoethyl)-2-methoxy-4-amino-5-chlorobenzamide (0.9 g), melting point: 145°–146° C. The product is identified with an authentic sample by infrared spectrum.

EXAMPLE 12

5-Chloro-2-benzothiazolinone-3-acetic acid (2.5 g) and triethylamine (1.4 ml) are dissolved in dichloromethane (25 ml). To the solution is added 1-methanesulfonyloxy-1,2,3-benzotriazole (2.2 g) at room temperature, and after 10 minutes, 1-(2-hydroxyethyl)piperazine (1.3 g) is thereto added. After allowing to stand at room temperature for 18 hours, the reaction mixture is washed with a saturated aqueous sodium hydrogen carbonate and then dried over magnesium sulfate. After drying, the solvent is distilled off and the resultig residue is crystallized from ethanol-ether. The crystals thus obtained are washed with acetone and dried to give 3-[4-(2-hydroxyethyl)-1-piperazinyl]carbonylmethyl-5-chloro-2-benzothiazolinone (1.3 g), melting point: 155°–156° C. The product is identified with an authentic sample by infrared spectrum.

EXAMPLE 13

2-Thienylacetic acid (4.2 g) and triethylamine (4.2 ml) are dissolved in dichloromethane (40 ml) and thereto is added at one time 1-methanesulfonyloxy-1,2,3-benzotriazole (6.2 g) with stirring at room temperature. The mixture is stirred at room temperature for 1 hour. The solution thus obtained is added at one time to a solution of 7-aminocephalosporanic acid (5.6 g) and triethylamine (8.4 ml) in dichloromethane (30 ml) at room temperature. The mixture is stirred for 2 hours and allowed to stand for 20 hours. After reaction, to the reaction mixture is added triethylamine (about 3 ml) and the mixture is extracted with water (50 ml, once; 25 ml, twice). The extract is regulated to pH 4.2 with acetic acid and passed through a column (inside diameter: 2.5 cm) containing Zeolite A-6 resin (75 ml). A 5% aqueous solution of sodium acetate and acetic acid (pH: 4.5, 400 ml) is passed through the column. The eluate thus obtained is extracted with ethyl acetate (100 ml) with making gradually acidic with 6 N hydrochloric acid. The extract is dried over anhydrous magnesium sulfate and then the solvent is distilled off under a reduced pressure. The resulting oily residue is crystallized from ether (about 50 ml). The crystals thus obtained is separated by filtration and dried to give 7-[2-(2-thienyl)acetamido]cephalosporanic acid (5.5 g, 70%), melting point: 135°–140° C. (decomp). The product is identified with an authentic sample by infrared spectrum.

EXAMPLE 14

N-Benzyloxycarbonyl-L-phenylalanine (1.5 g) and triethylamine (0.7 ml) are dissolved in anhydrous tetrahydrofuran (20 ml). To the solution is added 1-methanesulfonyloxy-1,2,3-benzotriazole (1.10 g) at room temperature and the mixture is stirred for 1 hour, and thereto is further added 28% aqueous ammonia (3.0 ml) and the mixture is stirred for 2 hours. After allowing to stand, the solvent is distilled off under a reduced pressure, and to the residue is added water and the crystals are crushed. The crystals are separated by filtration, washed with water and dried to give N-benzyloxycarbonyl-L-phenylalaninamide (1.15 g), melting point: 158°–160° C. The product is identified with an authentic sample by infrared spectrum.

EXAMPLE 15

N-Benzyloxycarbonyl-L-valine (1.25 g) and L-valine ethyl ester hydrochloride (1.08 g) are dissolved in dichloromethane (15 ml) and thereto are added triethylamine (1.54 ml) and further 1-methanesulfonyloxy-1,2,3-benzotriazole (1.07 g) under ice-cooling. After allowing to stand at room temperature for 72 hours, to the reaction mixture are added water and ethyl acetate. The ethyl acetate layer is separated, washed with water, dried and then the solvent is distilled off to give N-(N-benzyloxycarbonyl-L-valyl)-L-valine ethyl ester (1.70 g). The product is washed with petroleum ether to give powdery product (1.50 g), melting point: 93°–93.5° C.

EXAMPLE 16

N-Benzyloxycarbonyl-L-phenylalanine (3.0 g) and L-isoleucine methyl ester hydrochloride (1.82 g) are dissolved in anhydrous dichloromethane (30 ml), and thereto are added triethylamine (2.80 ml) and further 1-methanesulfonyloxy-1,2,3-benzotriazole (2.15 g) with stirring under ice-cooling, and the mixture is stirred at room temperature for 40 hours. After reaction, the solvent is distilled off and the resulting residue is extracted with ethyl acetate. The extract is washed with water, a saturated aqueous sodium hydrogen carbonate (5 times), water, 2 N hydrochloric acid and water in order and then dried over anhydrous magnesium sulfate. After drying, the solvent is distilled off to give crystalline powder of N-(N-benzyloxycarbonyl-L-phenylalanyl)-L-isoleucine methyl ester (3.46 g), melting point: 94.5°–95.5° C.

EXAMPLE 17

N-Benzyloxycarboyl-L-proline (1.25 g), L-serine methyl ester hydrochloride (0.78 g) and triethylamine (1.40 ml) are dissolved in anhydrous chloroform (20 ml), and thereto is added 1-benzenesulfonyloxy-6-chloro-1,2,3-benzotriazole (1.5 g) with stirring under ice-cooling. After the mixture is stirred for 1 hour and then allowed to stand overnight, to the reaction mixture are added water and ethyl acetate. The ethyl acetate layer is separated, washed and then dried. After drying, the solvent is distilled off and the resulting oily residue is allowed to stand. To the crystals thus produced are added ether and petroleum ether and then the crystals are separated by filtration to give N-(N-benzyloxycarbonyl-L-prolyl)-L-serine methyl ester (1.5 g), melting point: 97°–100° C.

EXAMPLE 18

N-(N-Benzyloxycarboylglycyl)-L-phenylalanine (0.9 g), glycine ethyl ester hydrochloride (0.35 g) and triethylamine (0.70 ml) are dissolved in anhydrous chloroform (10 ml), and thereto is added 1-methanesulfonyloxy-1,2,3-benzotriazole (0.55 g) at room temperature. The mixture is stirred for 1 hour and allowed to stand overnight. To the reaction mixture are added water and ethyl acetate. The ethyl acetate layer is separated, washed with water, a saturated aqueous sodium hydrogen carbonate, water, 1 N hydrochloric acid and water in order and then dried over anhydrous magnesium sulfate. After drying, the solvent is distilled off, and the resulting crude crystals are recrystallized from ethanol to give N-[N-(N-benzyloxycarbonylglycyl)-L-phenylalanyl]glycine ether ester (0.80 g), melting point: 116°–118° C.

EXAMPLE 19

N-Benzyloxycarbonyl-L-valine (1.26 g), glycine ethyl ester hydrochloride (0.70 g) and triethylamine (1.40 ml) are dissolved in anhydrous chloroform (10 ml), and thereto is added 1-methanesulfonyloxy-1,2,3-benzotriazole (1.05 g) with stirring under ice-cooling. After stirrig at room temperature for 20 hours, to the reaction mixture are added water and ethyl acetate. The ethyl acetate layer is separated, washed and dried. After drying, the solvent is distilled off to give N-(N-benzyloxycarbonyl-L-valyl)glycine ethyl ester hydrochloride (1.1 g), melting point: 162°–165° C.

EXAMPLE 20

$N^\alpha$-Tert.-butoxycarbonyl-$N^G$-nitro-L-arginine (1.60 g) and L-tyrosine benzyl ester p-toluenesulfonate (2.22 g) are dissolved in anhydrous chloroform (20 ml), and thereto are added triethylamine (1.40 ml) and further 1-methanesulfonyloxy-1,2,3-benzotriazole (1.05 g) and the mixture is stirred at room temperature for 20 hours. After the reaction, to the reaction mixture are added ethyl acetate and water. The ethyl acetate layer is separated, washed with water, a saturated aqueous sodium hydrogen carbonate, water, an aqueous citric acid solution and water in order and then dried over anhydrous magnesium sulfate. After drying, the solvent is distilled off, and the resulting residue is dissolved in chloroform, subjected to chromatography by using silica gel (20 g) and eluted with chloroform to give amorphous powder of N-(N$^\alpha$-tert.-butoxycarbonyl-N$^G$-nitro-L-arginyl)-L-tyrosine benzyl ester (2.0 g).

Anal. Calcd. for $C_{27}H_{36}O_8N_6 \cdot 1/2H_2O$: C,55.75; H,6.41; N,14.47. Found: C,55.95; H,6.41; N,14.14.

EXAMPLE 21

L-Histidine methyl ester dihydrochloride (1.21 g) is suspended into chloroform (20 ml), and therto are added triethylamine (1.40 ml) and further N-benzyloxycarbonyl-L-glutamine (1.40 g) and triethylamine (0.70 ml). After stirring for a while, to the mixture is added 1-methanesulfonyloxy-1,2,3-benzotriazole (1.07 g) and the mixture is stirred for 1 hour. After allowing to stand overnight, the solvent is distilled off. To the residue are added water and 1 N aqueous sodium hydrogen carbonate and the mixture is cooled. The precipitated gelling product is separated by filtration and washed with water. The product is heated together with a small amount of water and cooled. The precipitated by filtration to give N-(N-benzyloxycarbonyl-L-glutaminyl)-L-histidine methyl ester (1.25 g), melting point: 186°–188° C.

Anal. Calcd. for $C_{20}H_{25}O_6N_5$: C,55,67; H,5.84; N,16.24. Found: C,55,53; H,5.81; N,16.22.

EXAMPLE 22

2-Methoxy-5-sulfamoylbenzoic acid (2.3 g) and triethylamine (1.4 ml) are dissolved in anhydrous tetrahydrofuran (20 ml), and therto is added 1-methanesulfonyloxy-1,2,3-benzotriazole (2.2 g). After stirring at room temperature for 20 minutes, to the mixture is added 1-ethyl-2-aminomethylpyrrolidine (1.3 g) to precipitate oily products with exotherm. The mixture is stirred for 1 hour and then the solvent is distilled off. The resulting oily residue is dissolved in 1 N hydrochloric acid and the solution is washed twice with ethyl acetate. The aqueous layer is distilled under a reduced pressure to remove the remaining ethyl acetate and made alkaline with aqueous ammonia. The resulting precipitates are separated by filtration, washed with diluted aqueous ammonia and dried to give 1-ethyl-2-(2-methoxy-5-sulfamoylbenzamidomethyl)pyrrolidine (2.2 g), melting point: 175°–177° C.

EXAMPLE 23

N-Benzyloxycarbonyl-L-glutamine (1.40 g) and triethylamine (0.7 ml) are dissolved in anhydrous acetonitrile (10 ml) and thereto is added 1-n-butanesulfonyloxy-6-chloro-1,2,3-benzotriazole (1.47 g) at room temperature, whereby crystals are precipitated. After 30 minutes, to the mixture is added a solution of L-tyrosine benzyl ester p-toluenesulfonate (2.2 g) and triethylamine (0.7 ml) in anhydrous acetonitrile (20 ml) and the mixture is stirred, by which the crystals are dissolved to give a homogeneous solution. The solution is further stirred for 3 hours to precipitate gel materials. After allowing to stand overnight, to the reaction mixture is added water, and the mixture is concentrated under a reduced pressure. To the resulting residue are added water and ethyl acetate and then the mixture is filtered to give N-(N-benzyloxycarbonyl-L-glutaminyl)-L-tyrosine benzyl ester (1.275 g), melting point: 165°–170° C.

The ethyl acetate layer obtained above by filtration is washed with 1 N hydrochloric acid, aqueous sodium hydrogen carbonate and water in order and dried over anhydrous magnesium sulfate, and then the solvent is distilled off to give additionally the desired product (0.642 g), melting point: 164°–167° C. The product is recrystallized from methanol to give a pure product having a melting point of 173°–174° C.

EXAMPLE 24

N-Benzyloxycarbonyl-L-proline (1.25 g), L-leucine ethyl ester hydrochloride (1.00 g) and N-methylmorpholine (1.10 ml) are dissolved in chloroform (10 ml) and thereto is added 4-oxo-3,4-dihydro-3-methanesulfonyloxy-1,2,3-benzotriazine (1.20 g). After allowing to stand overnight, to the mixture are added water and ethyl acetate. The ethyl acetate layer is washed and dried, and then the solvent is distilled off to give N-(N-benzyloxycarbonyl-L-prolyl)-L-leucine ethyl ester (1.3 g), melting point: 65°–67° C.

EXAMPLE 25

N-Benzyloxycarbonyl-L-proline (1.25 g), L-serine methyl ester hydrochloride (0.78 g) and triethylamine (1.40 ml) are dissolved in dry chloroform (20 ml) and thereto is added 1-(p-chlorobenzenesulfonyloxy)-6-chloro-1,2,3-benzotriazole (1.72 g) under ice-cooling. After allowing to stand overnight, to the mixture are added water and ethyl acetate. The ethyl acetate layer is washed and dried, and then the solvent is distilled off to give N-(N-benzyloxycarbonyl-L-prolyl)-L-serine methyl ester (1.4 g), melting point: 96°–100° C.

EXAMPLE 26

N-(N-Benzyloxycarbonyl-L-prolyl)-L-leucine (4.6 g), glycine ethyl ester hydrochloride (1.8 g) and triethylamine (1.78 ml) are dissolved in dry chloroform (40 ml) and thereto is added 1-(p-toluenesulfonyloxy)-6-nitro-1,2,3-benzotriazole (4.25 g) under ice-cooling and the mixture is stirred for 1 hour. After allowing to stand overnight, to the mixture are added water and ethyl acetate. The ethyl acetate layer is washed with 1 N aqueous ammonia containing 5% NaCl (six times), water, 1 N hydrochloric acid and water in order, dried over anhydrous magnesium sulfate, and then the solvent is distilled off. The resulting residue is washed with ether-petroleum ether to give N-[N-(N-benzyloxycarbonyl-L-prolyl)-L-leucyl]glycine ethyl ester (3.0 g), melting point: 149°–150° C.

EXAMPLE 27

In the same manner as described in the foregoing Examples, the amidation reaction is carried out by using the following various sulfonic acid esters, which gives the similar results.

2-Methanesulfonyloxyimino-2-cyanoacetamide, melting point: 143°–145° C.

N-Methanesulfonyloxysuccinimide, melting point: 150°–152° C.

1-Methanesulfonyloxy-6-nitro-1,2,3-benzotriazole, melting point: 117°–118° C.

1-Methanesulfonyloxy-6-chloro-1,2,3-benzotriazole, melting point: 174°–175° C. (decomp)

1-Methanesulfonyloxy-4-chloro-1,2,3-benzotriazole, melting point: 71°–74° C.

1-(DL-10-Camphor-sulfonyloxy)-1,2,3-benzotriazole, melting point: 146°–148° C.
1-(DL-10-Camphor-sulfonyloxy)-6-nitro-1,2,3-benzotriazole, melting point: 157°–159° C.
1-(DL-10-Camphor-sulfonyloxy)-6-chloro-1,2,3-benzotriazole, melting point: 151°–153° C.
1-Benzylsulfonyloxy-1,2,3-benzotriazole, melting point: 65°–67° C.
1-Benzenesulfonyloxy-1,2,3-benzotriazole, melting point: 83°–84° C.
1-Benzenesulfonyloxy-6-nitro-1,2,3-benzotriazole, melting point: 124° C.
1-(p-Toluenesulfonyloxy)-1,2,3-benzotriazole, melting point: 85°–86° C.
1-(p-Chlorobenzenesulfonyloxy)-1,2,3-benzotriazole, melting point: 94°–95° C.
1-(p-Nitrobenzenesulfonyloxy)-1,2,3-benzotriazole, melting point: 119.5°–121.5° C.
1-(3-Pyridylsulfonyloxy)-1,2,3-benzotriazole, melting point: 98° C.
1-Mesitylenesulfonyloxy-1,2,3-benzotriazole, melting point: 130°–131° C.
1-(β-Styrenesulfonyloxy)-1,2,3-benzotriazole, melting point: 102°–103° C.
1-(n-Butanesulfonyloxy)-1,2,3-benzotriazole, oily substance, infrared spectrum (film): 1395, 1175 cm$^{-1}$
1-Benzylsulfonyloxy-6-chloro-1,2,3-benzotriazole, melting point: 126.5°–127.5° C.
1-(p-Toluenesulfonyloxy)-6-chloro-1,2,3-benzotriazole, melting point: 94°–96° C.
1-(p-Vinylbenzenesulfonyloxy)-6-vinyl-1,2,3-benzotriazole, melting point: 85°–87° C.
1-(p-Chlorobenzenesulfonyloxy)-6-vinyl-1,2,3-benzotriazole, melting point: 125° C.
1-(p-Toluenesulfonyloxy)-6-vinyl-1,2,3-benzotriazole, melting point: 90°–91° C.
1-Methanesulfonyloxy-6-vinyl-1,2,3-benzotriazole, melting point: 129°–129.5° C.
4-Oxo-3,4-dihydro-3-benzenesulfonyloxy-1,2,3-benzotriazine, melting point: 132°–134° C.

The esterification of the present invention is illustrated by the following Examples.

EXAMPLE 38

N-Benzyloxycarbonyl-L-phenylalanine (1.5 g) and triethylamine (0.7 ml) are dissolved in ethyl acetate (15 ml). To the solution is added 1-methanesulfonyloxy-1,2,3-benzotriazole (1.1 g) under ice-cooling and the mixture is stirred for 1 hour. After allowing to stand overnight, to the reaction mixture are added ethyl acetate and water. The ethyl acetate layer is separated, washed with water and dried over anhydrous magnesium sulfate. After drying, the solvent is distilled off and to the residue is added ether. The precipitated crystals are separated by filtration to give 1-(N-benzyloxycarbonyl-L-phenylalanyloxy)-1,2,3-benzotriazole (1.3 g), melting point: 120°–125° C.

EXAMPLE 29

N-Benzyloxycarbonyl-L-valine (1.26 g) and triethylamine (0.70 ml) are dissolved in ethyl acetate (10 ml). To the solution is added ethyl 2-methanesulfonyloxyimino-2-cyanoacetate (1.1 g) and the mixture is stirred at room temperature for 20 hours. The reaction mixture is washed with water, dried and then concentrated to give ethyl 2-(N-benzyloxycarbonyl-L-valyloxyimino)-2-cyanoacetate (1.8 g) as an oily substance.

EXAMPLE 30

N-Benzyloxycarbonyl-L-proline (1.25 g) and ethyl 2-methanesulfonyloxyimino-2-cyanoacetate (1.1 g) are dissolved in ethyl acetate (10 ml). To the solution is added triethylamine (0.7 ml) and the mixture is stirred at room temperature for 1 hour. After allowing to stand overnight, to the reaction mixture is added ethyl acetate. The mixture is washed with water and dried over anhydrous magnesium sulfate. After drying, the solvent is distilled off to give ethyl 2-(N-benzyloxycarbonyl-L-prolyloxyimino)-2-cyanoacetate (1.9 g) as an oily substance.

EXAMPLE 31

To a solution of benzoic acid (2.5 g) and triethylamine (5.6 ml) in methanol (5.0 ml) and anhydrous ether (30 ml) is added 1-methanesulfonyloxy-1,2,3-benzotriazole (4.3 g) under cooling. The mixture is stirred for 1 hour and then allowed to stand overnight. The reaction mixture is extracted with ether, and the extract is washed with water, an aqueous sodium hydrogen carbonate and water in order, dried over anhydrous magnesium sulfate and then the solvent is distilled off to give methyl benzoate (2.1 g) as an oily substance.

EXAMPLE 32

(a) Benzoic acid (2.44 g) is dissolved in chloroform (30 ml), and thereto are added triethylamine (2.80 ml) under ice-cooling and further 1-(p-chlorobenzenesulfonyloxy)-1,2,3-benzotriazole (6.2 g) at room temperature, and the mixture is stirred for 2 hours. After the reaction, chloroform is distilled off, and to the resulting residue are added water and ethyl acetate. The ethyl acetate layer is washed with water, an aqueous sodium hydrogen sulfate and water in order and dried over anhydrous magnesium sulfate. After drying, the solvent is distilled off to give yellow crystals of 1-benzoyloxy-1,2,3-benzotriazole (3.9 g). The product is recrystallized from isopropanol to give faint yellow crystals of the product, melting point: 75°–78.5° C.

(b) Benzoic acid (2.44 g) is dissolved in a solution of triethylamine (2.80 ml) in dichloromethane (20 ml) under ice-cooling. To the solution is added 1-methanesulfonyloxy-1,2,3-benzotriazole (4.26 g) and the mixture is stirred at room temperature for 3 hours. The reaction mixture is washed with water, a saturated aqueous sodium hydrogen carbonate and water in order and dried to give crystals of 1-benzoyloxy-1,2,3-benzotriazole (5.0 g). The product is dissolved in dichloromethane (20 ml) and thereto are added triethylamine (2.80 ml) and methanol (4.8 ml) and the mixture is stirred at room temperature for 1 hour. The reaction mixture is washed with water, an aqueous sodium hydrogen carbonate and water in order, dried and then the solvent is distilled off to give methyl benzoate (2.39 g). Infrared spectrum: 1728 cm$^{-1}$.

EXAMPLE 33

(a) Benzoic acid (2.4 g) is dissolved in dichloromethane (30 ml), and thereto are added triethylamine (2.8 ml) and further 1-(p-chlorobenzenesulfonyloxy)-6-chloro-1,2,3-benzotriazole (6.9 g) and the mixture is stirred for 4 hours. After the reaction, dichloromethane is distilled off and to the resulting residue are added water and ethyl acetate. The ethyl acetate layer is washed with water, an aqueous sodium hydrogen carbonate and water in order, dried over anhydrous magnesium sulfate and the solvent is distilled off to give white crystals of 1-benzoyloxy-6-chloro-1,2,3-benzotriazole (4.55 g). The product is recrystallized from ethanol to give pure product, melting point: 132° C.

(b) To a solution of benzoic acid (1.22 g) and triethylamine (1.4 ml) in chloroform (15 ml) is added 1-(p-chlorobenzenesulfonyloxy)-6-chloro-1,2,3-benzotriazole (3.44 g) and the mixture is allowed to stand for 1.5 hours. To the mixture are added methanol (1.6 ml) and triethylamine (1.4 ml), whereby exothermic reaction occurrs. After reacting them for 1 hour and 20 minutes, chloroform is distilled off and to the resulting residue are added water and ether. The ether layer is washed with water, an aqueous sodium hydrogen carbonate and water in order and dried over anhydrous magnesium sulfate. After drying, the solvent is distilled off to give methyl benzoate (1.26 g).

EXAMPLE 34

Heptanoic acid (1.30 g) is dissolved in chloroform (15 ml) and thereto are added triethylamine under ice-cooling and further 1-(p-chlorobenzenesulfonyloxy)-6-chloro-1,2,3-benzotriazole (3.44 g), and the mixture is stirred for 3 hours. To the solution are added methanol (0.61 ml) and triethylamine (1.40 ml), whereby exothermic reaction occurs. After stirring for 10 minutes, chloroform is distilled off and to the resulting residue are added water and ether. The ether layer is washed with water, an aqueous sodium hydrogen carbonate and water in order, dried over anhydrous magnesium sulfate and the solvent is distilled off to give methyl heptanoate (1.25 g).

EXAMPLE 35

(a) Tetrazolacetic acid (6.4 g) is suspended into chloroform (100 ml) and thereto is added triethylamine (7.0 ml) under ice-cooling. The mixture is stirred at room temperature until it becomes a homogeneous solution. To the solution is added 1-(p-chlorobenzenesulfonyloxy)-6-chloro-1,2,3-benzotriazole (17.2 g). When the mixture is stirred at room temperature for 30 minutes, while crystals precipitate. The mixture is further stirred for 48 hours, and the precipitated crystals are separated by filtration, washed with anhydrous chloroform and dried to give 1-[2-(1H-tetrazol-1-yl)acetoxy]-6-chloro-1,2,3-benzotriazole (9.7 g), melting point: 171°–172° C. (decomp).

(b) Tetrazolacetic acid (1.28 g) is suspended into chloroform and thereto is added triethylamine (1.40 ml) under ice-cooling to give a homogeneous solution. To the solution is added 1-(p-chlorobenzenesulfonyloxy)-6-chloro-1,2,3-benzotriazole (3.44 g), and the mixture is stirred at room temperature to precipitate clear crystals. After stirring overnight, to the mixture are added benzyl alcohol (1.55 ml) and triethylamine (1.4 ml), whereby the crystals dissolve with exotherm. After stirring at room temperature for 3 hours, chloroform is distilled off and to the resulting residue are added water and ethyl acetate. The ethyl acetate layer is washed with water, an aqueous sodium hydrogen carbonate, 1 N hydrochloric acid and a saturated aqueous sodium chloride and dried over anhydrous magnesium sulfate. After drying, the solvent is distilled off and the residue is allowed to stand. The resulting crystals are washed with ether and recrystallized from isopropyl alcohol to give benzyl tetrazolacetate (1.4 g), melting point: 72°–73° C.

Anal. Calcd. for $C_{10}H_{10}O_2N_4$: C,55.04; H,4.62; N,25.68. Found: C,55.27; H,4.53; N,25.89.

EXAMPLE 36

(a) p-Nitrobenzoic acid (1.67 g) is dissolved in chloroform (20 ml) and thereto are added triethylamine (1.40 ml) under ice-cooling and further 1-(p-chlorobenzenesulfonyloxy)-6-chloro-1,2,3-benzotriazole (3.44 g) at room temperature. When the mixture is stirred at room temperature for 20 minutes, white crystals precipitate, and the mixture is further stirred for 7 hours. The precipitated crystals are separated by filtration to give white crystals of 1-(p-nitrobenzoyloxy)-6-chloro-1,2,3-benzotriazole (2.4 g), melting point: 198°–199° C. (decomp).

(b) p-Nitrobenzoic acid (1.67 g) is suspended into chloroform (20 ml) and thereto are added triethylamine (1.40 ml) under ice-cooling and further 1-(p-chlorobenzenesulfonyloxy)-6-chloro-1,2,3-benzotriazole (3.44 g). When the mixture is stirred at room temperature for 15 minutes, yellow precipitates are produced and the mixture is further stirred for 5 hours. To the mixture are added methanol (0.6 ml) and triethylamine (1.4 ml), whereby the precipitates are dissolved. After stirring for 1 hour, chloroform is distilled off and the residue extracted with ethyl acetate. The extract is washed with water, an aqueous sodium hydrogen carbonate, 1 N hydrochloric acid and water in order and dried over anhydrous magnesium sulfate. After drying, the solvent is distilled off. The resulting crystals aare recrystallized from isopropyl alcohol to give yellow crystals of methyl p-nitrobenzoate (1.4 g), melting point: 93°–94° C.

EXAMPLE 37

3-Acetoxymethyl-7-[2-(2-thienyl)acetamido]-3-cephem-4-carboxylic acid (1.98 g) is suspended into acetonitrile (20 ml) and thereto are added triethylamine (0.7 ml) under ice-cooling and further 1-(p-chlorobenzenesulfonyloxy)-6-chloro-1,2,3-benzotriazole (1.72 g). When the mixture is stirred at room temperature for 20 minutes, insoluble substance are produced and then acetonitrile (10 ml) is further added thereto. The mixture is stirred for 1.5 hours and thereto are added methanol (0.24 ml) and triethylamine (0.7 ml) to give a homogeneous deep violet solution. After stirring for 30 minutes, acetonitrile is distilled off and to the residue are added water and chloroform. The chloroform layer is washed with water, an aqueous sodium hydrogen carbonate, 1 N hydrochloric acid and an aqueous sodium chloride in order and dried over anhydrous magnesium sulfate. After drying, the mixture is treated with charcoal and then the solvent is distilled off to give an oily substance (2.1 g). The product is crystallized from ether-petroleum ether to give methyl 3-acetoxy-methyl-7-[2-(2-thienyl)acetamido]-2-cephem-4-carboxylate (1.39 g), melting point: 110°–121° C.

EXAMPLE 38

Tetrazole-1-acetic acid (0.64 g), benzyl alcohol (0.65 g) and pyridine (0.80 ml) are dissolved in dry cyanomethane (10 ml) and thereto is added 1-(p-chlorobenzenesulfonyloxy)-6-chloro-1,2,3-benzotriazole (1.72 g) under ice-cooling. After allowing to stand overnight, to the mixture are added water and ethyl acetate. The ethyl acetate layer is washed, dried and concentrated. The precipitated crystals are washed well with ether-petroleum ether to give benzyl tetrazole-1-acetate (815 mg), melting point: 69°–72° C.

EXAMPLE 39

In the same manner as described in the foregoing Examples 28 to 38, the esterification reaction is carried out by using the following various sulfonic acid esters, which gives the similar results.

Ethyl 2-methanesulfonyloxyimino-2-cyanoacetate, melting point: 79°–81.5° C.

2-Methanesulfonyloxyimino-2-cyanoacetamide, melting point: 143°–145° C.

N-Methanesulfonyloxysuccinimide, melting point: 150°–152° C.

1-Methanesulfonyloxy-6-nitro-1,2,3-benzotriazole, melting point: 117°–118° C.

1-Methanesulfonyloxy-6-chloro-1,2,3-benzotriazole, melting point: 174°–175° C. (decomp)

1-Methanesulfonyloxy-4-chloro-1,2,3-benzotriazole, melting point: 71°–74° C.

1-(DL-10-Camphor-sulfonyloxy)-1,2,3-benzotriazole, melting point: 146°–148° C.

1-(DL-10-Camphor-sulfonyloxy)-6-nitro-1,2,3-benzotriazole, melting point: 157°–159° C.

1-(DL-10-Camphor-sulfonyloxy)-6-chloro-1,2,3-benzotriazole, melting point: 151°–153° C.

1-Benzylsulfonyloxy-1,2,3-benzotriazole, melting point: 65°–67° C.

Ethyl 2-(p-toluenesulfonyloxyimino)-2-cyanoacetate, melting point: 84°–87° C.

1-Benzenesulfonyloxy-1,2,3-benzotriazole, melting point: 83°–84° C.

1-Benzenesulfonyloxy-6-nitro-1,2,3-benzotriazole, melting point: 124° C.

1-(p-Toluenesulfonyloxy)-1,2,3-benzotriazole, melting point: 85°–86° C.

1-Benzenesulfonyloxy-6-chloro-1,2,3-benzotriazole, melting point: 110°–110.5° C.

1-(p-Toluenesulfonyloxy)-6-nitro-1,2,3-benzotriazole, melting point: 144° C.

1-(p-Chlorobenzenesulfonyloxy)-1,2,3-benzotriazole, melting point: 94°–95° C.

1-(p-Nitrobenzenesulfonyloxy)-1,2,3-benzotriazole, melting point: 119.5°–121.5° C.

1-(3-Pyridylsulfonyloxy)-1,2,3-benzotriazole, melting point: 98° C.

1-Mesitylenesulfonyloxy-1,2,3-benzotriazole, melting point: 130°–131° C.

1-($\beta$-Styrenesulfonyloxy)-1,2,3-benzotriazole, melting point: 102°–103° C.

1-(n-Butanesulfonyloxy)-1,2,3-benzotriazole, oily substance, infrared spectrum (film): 1395, 1175 cm$^{-1}$ 1-(n-Butanesulfonyloxy)-6-chloro-B 1,2,3-benzotriazole, melting point: 72°–74° C.

1-Benzylsulfonyloxy-6-chloro-1,2,3-benzotriazole, melting point: 126.5°–127.5° C.

1-(p-Toluenesulfonyloxy)-6-chloro-1,2,3-benzotriazole, melting point: 94°–96° C.

1-(p-Vinylbenzenesulfonyloxy)-6-vinyl-1,2,3-benzotriazole, melting point: 85°–87° C.

1-(p-Chlorobenzenesulfonyloxy)-6-vinyl-1,2,3-benzotriazole, melting point: 125° C.

1-(p-Toluenesulfonyloxy)-6-vinyl-1,2,3-benzotriazole, melting point: 90°–91° C.

1-Methanesulfonyloxy-6-vinyl-1,2,3-benzotriazole, melting point: 129°–129.5° C.

4-Oxo-3,4-dihydro-3-methanesulfonyloxy-1,2,3-benzotriazine, melting point: 132°–134° C.

4-Oxo-3,4-dihydro-3-benzenesulfonyloxy-1,2,3-benzotriazine, melting point: 132°–134° C.

The preparation of the novel sulfonic acid esters of the present invention is illustrated by the following Examples. In the ultraviolet spectrum in the Examples, $\lambda$max means maximum absorption point and E means $E_{1\ cm}^{1\%}$.

EXAMPLE 40

Ethyl 2-hydroxyimino-2-cyanoacetate (7.1 g) and triethylamine (7.0 ml) are dissolved in benzene (50 ml). To the solution is added dropwise a solution of methanesulfonyl chloride (3.9 ml) in benzene (8 ml) with stirring under ice-cooling and the mixture is stirred at the temperature for 3 hours and then allowed to stand overnight. The reaction mixture is filtered to remove the precipitates and the filtrate is concentrated to give crystals of ethyl 2-methanesulfonyloxyimino-2-cyanoacetate (10.6 g; 96.3%), melting point: 79°–83° C. The product is recrystallized from benzene-petroleum ether to give crystals having a melting point of 79°–81.5° C.

Anal. Calcd. for $C_6H_8O_5N_2S$: C,32,37; H,3.66; N,12.72. Found: C,32.81; H,3.78; N,12.86.

EXAMPLE 41

Ethyl 2-hydroxyimino-2-cyanoacetate (28.4 g) and triethylamine (28.0 ml) are dissolved in benzene (150 ml). To the solution is added dropwise a solution of methanesulfonyl chloride (15.6 ml) in benzene (40 ml) with stirring under ice-cooling. After allowing to stand overnight, to the reaction mixture are added benzene (500 ml) and water (100 ml). The benzene layer is washed with water and dried over anhydrous magnesium sulfate. After drying, the solvent is distilled off and the residue is washed well with ether and petroleum ether to give ethyl 2-methane-sulfonyloxyimino-2-cyanoacetate (41.8 g; 95%), melting point: 78°–81° C.

EXAMPLE 42

Ethyl 2-hydroxyimino-2-cyanoacetate (28.4 g) and anhydrous potassium carbonate (13.8 g) are dissolved in water (100 ml) and thereto is added benzene (10 ml). To the mixture is added dropwise methanesulfonyl chloride (15.6 ml) with stirring under ice-cooling and the mixture is further stirred for 1 hour. After allowing to stand overnight, the reaction mixture is extracted with ethyl acetate (300 ml). The extract is washed with water and dried over anhydrous magnesium sulfate. After drying, the solvent is distilled off to give ethyl 2-methanesulfonyloxyimino-2-cyanoacetate (38.0 g; 86.3%), melting point: 79°–81° C.

EXAMPLE 43

2-Cyanoacetamide (8.4 g) and sodium nitrite (8.4 g) are dissolved in water (80 ml). To the solution is added dropwise acetic acid (11.8 g) under ice-cooling, and the mixture is stirred at a temperature of lower than 20° C. for 2 hours to give 2-hydroxyimino-2-cyanoacetamide. After allowing to stand overnight, to the reaction mixture is added ethyl acetate (40 ml). To the solution is added dropwise methanesulfonyl chloride (7.8 ml) under ice-cooling and the mixture is stirred at room temperature for 3 hours. The reaction mixture is extracted with dioxane and ethyl acetate. The extract is washed with water and concentrated. To the residue are added water and ethyl acetate, and the ethyl acetate layer is washed with water and dried over anydrous magnesium sulfate. After drying, the solvent is distilled off to give crystals of 2-methanesulfonyloxyimino-2-cyanoacetamide (14.6 g), melting point: 136°–142° C. The product is recrystallized from dioxane-ethyl acetate-petroleum ether to give a pure product, melting point: 143°–145° C.

Anal. Calcd. for $C_4H_5O_4N_3S$: C,25.13; H,2.64; N,21.99; S,16.77. Found: C,24.83; H,2.53; N,22.17; S,16.84.

EXAMPLE 44

N-Hydroxysuccinimide (11.5 g) and triethylamine (14.0 ml) are suspended into a mixture of benzene (100 ml) and dioxane (50 ml), and thereto is added dropwise a solution of methanesulfonyl chloride (7.8 ml) in benzene (20 ml) with stirring under ice-cooling and the mixture is stirred for 1 hour. After allowing to stand overnight, the solvent is distilled off. To the residue is added water and the resulting crystals are separated by filtration, washed with water and dried to give N-methanesulfonyloxysuccinimide (6.3 g), melting point: 148°–150° C. The product is recrystallized from ethyl acetate-petroleum ether to give crystals having a melting point of 150°–152° C.

Anal. Calcd. for $C_5H_7O_5NS$: C,31.08; H,3.65; N,7.25. Found: C,31.58; H,3.65; N,7.37.

EXAMPLE 45

1-Hydroxy-1,2,3-benzotriazole (6.5 g) and trimethylamine (7.0 ml) are dissolved in benzene (50 ml). To the solution is added dropwise methanesulfonyl chloride (3.9 ml) with stirring under ice-cooling and the mixture is stirred for 2 hours and then allowed to stand overnight. To the reaction mixture are added water and ethyl acetate. The ethyl acetate layer is washed with water and dried over anhydrous magnesium sulfate. After drying, the solvent is distilled off. The resulting crystals are washed with petroleum ether to give 1-methanesulfonyloxy-1,2,3-benzotriazole (9.2 g), melting point: 90°–92° C.

Anal. Calcd. for $C_7H_7O_3N_3S$: C,39.43; H,3.31; N,19.71; S,15.03. Found: C,39.72; H,3.20; N,20.14; S,15.04.

EXAMPLE 46

1-Hydroxy-1,2,3-benzotriazole (648 g) and triethylamine (675 ml) are dissolved in benzene (2,800 ml). To the solution is added dropwise a solution of methanesulfonyl chloride (535 g) in benzene (675 ml) with stirring at a temperature of lower than 10° C. over a period of 2.2 hours. The mixture is stirred at the same temperature for 2.3 hours and allowed to stand overnight. To the reaction mixture is added water (1,000 ml). The benzene layer is separated out. The aqueous layer is extracted twice with ethyl acetate (3,000 ml and 2,000 ml), and the extracts are combined and washed with a saturated aqueous sodium hydrogen carbonate (200 ml×2) and water and dried over anhydrous magnesium sulfate. After drying, the solvent is distilled off under a reduced pressure. The resulting crystals are washed with petroleum ether (500 ml) and dried to give faint yellow crystals of 1-methane-sulfonyloxy-1,2,3-benzotriazole (842 g), melting point: 88°–90° C.

Ultraviolet spectrum (methanol): λmax 256 nm, E=257; λmax 284 nm, E=176.

EXAMPLE 47

1-Hydroxy-1,2,3-benzotriazole (25.7 g) is suspended into water (50 ml) and thereto is added 1 N aqueous sodium hydroxide (180 ml). To the resulting solution is added dropwise methanesulfonyl chloride (14.0 ml) with stirring under ice-cooling and thereto is further added ethyl acetate (30 ml), and the mixture is stirred for 4 hours. The reaction mixture is extracted with ethyl acetate, and the extract is washed with water and dried over anhydrous magnesium sulfate. After drying, the solvent is distilled off and to the resulting residue is added petroleum ether, and the residue is cracked, filtered and dried to give 1-methanesulfonyloxy-1,2,3-benzotriazole (39.1 g), melting point: 88°–91° C.

EXAMPLE 48

1-Hydroxy-6-nitro-1,2,3-benzotriazole (7.2 g) is dissolved in 1 N aqueous sodium hydroxide (40 ml). To the solution is added dropwise methanesulfonyl chloride (5.6 g) with stirring under ice-cooling and thereto are added ethyl acetate (100 ml) and water (100 ml). The mixture is stirred at room temperature for 1 hour. To the reaction mixture is added ethyl acetate (50 ml) and the insoluble materials are filtered off. The ethyl acetate layer is dried over magnesium sulfate-charcoal. After drying, the layer is concentrated so as to be about 30 ml and thereto is added n-hexane (about 30 ml) and the mixture is allowed to stand. The precipitated crystals are separated by filtration and dried to give 1-methanesulfonyloxy-6-nitro-1,2,3-benzotriazole (7.3 g; 72%), melting point: 115°–116° c. The product is dissolved in ethyl acetate and treated with charcoal and thereto is added n-hexane to give faint yellow flakes melting point: 117°–118° C.

Anal. Calcd. for $C_7H_6O_5N_4S$: C, 32.57; H, 2.34; N, 21.70. Found: C, 32.74; H, 2.17; N, 21.95.

EXAMPLE 49

To pyridine-3-sulfonic acid (6 g) is added powdery phosphorus pentachloride (15.8 g) and the mixture is heated at 150° C. for 3 hours. The reaction mixture is concentrated under a reduced pressure at 60° to 70° C. and thereto is added anhydrous xylene. The mixture is concentrated under a reduced pressure and thereto is further added anhydrous xylene, and the mixture is again concentrated. To the resulting residue is gradually added water (20 ml) under cooling with dry ice-acetone to give a solution. The solution is added dropwise to a mixture of 1-hydroxy-1,2,3-benzotriazole (8.3 g), potassium carbonate (8.3 g), water (24 ml), benzene (40 ml) and ether (15 ml) at −2° to 0° C. with stirring. After the addition, to the mixture are added water (18 ml) and ether (15 ml) and the mixture is stirred at room temperature. The mixture is regulated at pH 7 to 8 with 1 N aqueous potassium hydroxide and then stirred for 2 hours. The reaction mixture is extracted with benzene-ether (240 ml). The extract is washed with a saturated aqueous sodium hydrogen carbonate and dried over potassium carbonate. After drying, the solvent is distilled off to give 1-(3-pyridylsulfonyloxy)-1,2,3-benzotriazole (7.2 g; 70%), melting point: 98° C.

Anal. Calcd. for $C_{11}H_8N_4O_3S$: C, 47.82; H, 2.92; N, 20.28. Found. C, 47.99; H, 2.81; N, 20.29.

EXAMPLE 50

To dichloromethane (70 ml) are added 1-hydroxy-6-nitro-1,2,3-benzotriazole (5.4 g) and further triethylamine (4.5 ml). To the resulting solution is added DL-10-camphor-sulfonyl-chloride (7.6 g) at room temperature with stirring and the mixture is stirred for 1 hour. The reaction mixture is washed four times with water (50 ml), dried over anhydrous magnesium sulfate and then the solvent is distilled off. The crystalline residue is washed with a mixture of n-hexane-ethyl acetate (1:1; 50 ml) and dried to give 1-(DL-10-camphor-sulfonyloxy)-6-nitro-1,2,3-benzotriazole (10.5 g). A part of the product is recrystallized from ethyl acetate-n-hexane to give colorless needles, melting point: 157°–159° C.

Anal. Calcd. for $C_{16}H_{18}O_6N_4S$: C, 48.72; H, 4.60; N, 14.21. Found: C, 48.65; H, 4.35; N, 14.23.

EXAMPLE 51

To benzene (14 ml) are added 1-hydroxy-4-chloro-1,2,3-benzotriazole (3.4 g) and further triethylamine (2.8 ml). To the solution is added methanesulfonyl chloride (2.3 g) with stirring under ice-cooling and the mixture is stirred at the same temperature for 20 minutes and further at room temperature for 1.5 hours. After allowing to stand overnight, to the reaction mixture are added water (20 ml) and ethyl acetate (30 ml) and the ethyl acetate layer is separated. The water layer is again extracted with ethyl acetate (20 ml). The ethyl acetate extracts are combined, washed with a small amount of a saturated aqueous sodium hydrogen carbonate and water in order, dried over anhydrous sodium sulfate and the solvent is distilled off under a reduced pressure. The residue is washed with petroleum ether (10 ml) to give faint yellow crystals of 1-methanesulfonyloxy-4-chloro-1,2,3-benzotriazole (3.89 g; 79%), melting point: 71°–74° C.

EXAMPLE 52

Into benzene (14 ml) is suspended 1-hydroxy-6-chloro-1,2,3-benzotriazole (3.4 g) and thereto is added triethylamine (2.8 ml). To the solution is added methanesulfonyl chloride (2.3 g) with stirring under ice-cooling and the mixture is stirred at the same temperature for 20 minutes and further at room temperature for 5 hours. To the reaction mixture are added water (20 ml) and ethyl acetate (30 ml) and the ethyl acetate layer is separated. the water layer is again extracted with ethyl acetate (20 ml). The ethyl acetate extracts are combined, washed with a small amount of a saturated aqueous sodium hydrogen carbonate and water in order and dried over anhydrous sodium sulfate. After drying, the solvent is distilled off under a reduced pressure, and the residue is washed with petroleum ether (10 ml) to give colorless crystals of 1-methanesulfonyloxy-6-chloro-1,2,3-benzotriazole (1.55 g), melting point: 174°–175° C. (decomp). The remaining water layer after extracted with ethyl acetate, wherein precipitates are observed, is regulated at pH 1 with concentrated hydrochloric acid. The precipitates are separated by filtration and washed with water to give the desired product (2.4 g) as colorless crystals, melting point: 157°–158° C. (decomp).

EXAMPLE 53

Into benzene (7 ml) is suspended 1-hydroxy-6-chloro-1,2,3-benzotriazole (396 mg) and thereto is added triethylamine (0.329 ml). To the solution is added dropwise a solution of DL-10-camphor-sulfonyl chloride (590 mg) in benzene (4 ml) with stirring under ice-cooling. The mixture is stirred at the same temperature for 1 hour and further at room temperature for 4 hours. To the reaction mixture are added water (10 ml) and ethyl acetate (50 ml). The ethyl acetate layer is washed with a saturated aqueous sodium hydrogen carbonate and water in order and dried over anhydrous sodium sulfate. After drying, the solvent is distilled off and the resulting residue is recrystallized from benzene-n-hexane to give 1-(DL-10-camphor-sulfonyloxy)-6-chloro-1,2,3-benzotriazole (610 mg), melting point: 151°–153° C. Ultraviolet spectrum (methanol): λmax 270 mµ, E=201.

Anal. Calcd. for $C_{16}H_{18}O_4N_3SCl$: C, 50.04; H, 4.73; N, 10.94. Found: C, 50.27; H, 4.72; N, 10.98.

EXAMPLE 54

In 1 N aqueous sodium hydroxide (50 ml) is dissolved 1-hydroxy-1,2,3-benzotriazole (5 g) and thereto is added ether (25 ml). To the solution is added benzylsulfonyl chloride (8 g) with stirring under ice-cooling. The mixture is stirred at the same temperature for 3 hours. The reaction mixture is extracted with ethyl acetate. The extract is washed with a saturated aqueous sodium hydrogen carbonate and water in order and dried over anhydrous magnesium sulfate. After drying, the solvent is distilled off and the oily residue is allowed to stand. The resulting crystals are recrystallized from benzene-petroleum ether to give 1-benzylsulfonyloxy-1,2,3-benzotriazole (5.0 g), melting point: 65°–67° C.

Anal. Calcd. for $C_{13}H_{11}N_3O_3S$: C, 53.97; H, 3.83; N, 14.52. Found: C, 54.08; H, 3.71; N, 14.28.

EXAMPLE 55

In dichloromethane (100 ml) are dissolved 1-hydroxy-1,2,3-benzotriazole (5.4 g) and triethylamine (5.6 ml). To the solution is added β-styrenesulfonyl chloride (8.0 g) with stirring at room temperature, and the mixture is stirred for 1 hour. The reaction mixture is washed twice with water (30 ml) and dried over anhydrous magnesium sulfate-charcoal. After drying, the solvent is distilled off. The residue is dissolved in ethyl acetate (20 ml) and thereto is added n-hexane (50 ml) to give needles of 1-(β-styrenesulfonyloxy)-1,2,3-benzotriazole (9.0 g). A part of the product is recrystallized from ethyl acetate-n-hexane to give a pure product, melting point: 102°–103° C.

Anal. Calcd. for $C_{14}H_{11}O_3N_3S$: C, 55.81; H, 3.68; N, 13.95. Found. C, 55.98; H, 3.58; N, 14.18.

EXAMPLE 56

In dichloromethane (30 ml) are dissolved 1-hydroxy-1,2,3-benzotriazole (2.7 g) and triethylamine (2.8 ml). To the solution is added DL-10-camphor-sulfonyl chloride (5.0 g) with stirring at room temperature and the mixture is stirred for 30 minutes. The reaction mixture is washed with water containing a small amount of triethylamine and water in order and dried over anhydrous magnesium sulfate. After drying, the solvent is distilled off, and the residue is washed with ethyl acetate-n-hexane to give 1-(DL-10-camphor-sulfonyloxy)-1,2,3-benzotriazole (2.5 g), melting point: 146°–148° C. A part of the product is recrystallized from ethyl acetate-n-hexane to give a pure product, melting point: 148°–150° C.

Anal. Calcd. for $C_{16}H_{19}O_4N_3S$: C, 54.99; H, 5.48; N, 12.03. Found: C, 54.77; H, 5.30; N, 12.12.

EXAMPLE 57

In dichloromethane (20 ml) are added 1-hydroxy-1,2,3-benzotriazole (2.70 g) and methanesulfonic acid (1.92 g) and thereto is added triethylamine (5.6 ml). To the solution is added dropwise thionyl chloride (1.43 ml) with stirring under ice-cooling during 15 minutes. The mixture is stirred at the same temperature for 1 hour and 10 minutes and at room temperature for 7 hours and 45 minutes, and then allowed to stand overnight. Dichloromethane is distilled off under a reduced pressure. To the residue are added water (30 ml) and ethyl acetate (100 ml). The ethyl acetate layer is washed with a saturated aqueous sodium hydrogen carbonate and water in order and dried over anhydrous sodium sulfate. After drying, the solvent is distilled off. To the residue is added petroleum ether and the mixture is filtered to give 1-methanesulfonyloxy-1,2,3-benzotriazole (1.2 g).

EXAMPLE 58

In benzene (50 ml) are dissolved 1-hydroxy-1,2,3-benzotriazole (6.8 g) and triethylamine (7.0 ml) and thereto is added dropwise a solution of n-butanesulfonyl chloride (7.8 g) in benzene (10 ml) at room temperature and the mixture is stirred for 4 hours. After the reaction, the benzene layer is separated, washed with water, dried over anhydrous magnesium sulfate and then concentrated to give 1-(n-butanesulfonyloxy)-1,2,3-benzotriazole (12.3 g) as an oily substance. Infrared spectrum (film): 1395, 1175 cm$^{-1}$.

EXAMPLE 59

In 1 N aqueous sodium hydroxide (50 ml) is dissolved 1-hydroxy-6-chloro-1,2,3-benzotriazole (8.5 g) and thereto is added dropwise a solution of n-butanesulfonyl chloride (7.8 g) in ethyl acetate (50 ml) at room temperature and the mixture is stirred for 2 hours. The reaction mixture is extracted with ethyl acetate. The extract is washed with water, dried over anhydrous magnesium sulfate and then concentrated to give crystals (14.2 g). The crystals are recrystallized from carbon tetrachloride-petroleum ether to give 1-(n-butanesulfonyloxy)-6-chloro-1,2,3-benzotriazole (12.3 g), melting point: 72°–74° C.

Anal. Calcd. for $C_{10}H_{12}N_3O_3SCl$: C, 41.45; H, 4.18; N, 14.50. Cl, 12.23. Found: C, 41.33; H, 4.06; N, 14.39; Cl, 12.32.

EXAMPLE 60

In 1 N aqueous sodium hydroxide (13.0 ml) and water is dissolved 1-hydroxy-6-chloro-1,2,3-benzotriazole (2.23 g) and thereto is added dropwise a solution of benzylsulfonyl chloride (2.5 g) in ether (50 ml) under ice-cooling and stirring, and the mixture is stirred at the same temperature for 1.5 hours and further at room temperature for 1 hour. The reaction mixture is distilled to remove ether. To the resulting residue is added ethyl acetate. The ethyl acetate layer is dried and distilled to remove the solvent. The residue is recrystallized from benzene-n-hexane to give white needles of 1-benzylsulfonyloxy-6-chloro-1,2,3-benzotriazole (2.4 g), melting point: 126.5°–127.5° C.

Anal. Calcd. for $C_{13}H_{10}N_3O_3SCl$: C, 48.23; H, 3.11; N, 12.98; S, 9.91; Cl, 10.95. Found: C, 48.04; H, 3.08; N, 12.85; S, 10.07; Cl, 10.91.

EXAMPLE 61

In benzene (30 ml) are dissolved 4-oxo-3,4-dihydro-3-hydroxy-1,2,3-benzotriazine (2.4 g) and triethylamine (2.1 ml) and thereto is added dropwise methanesulfonyl chloride (1.7 g), whereby faint exotherm occurs and crystals are precipitated. The reaction mixture is extracted with ethyl acetate (80 ml). The extract is washed with water, an aqueous sodium hydrogen carbonate and water in order, dried over anhydrous magnesium sulfate and then distilled to remove the solvent. The resulting residue is washed with ether-petroleum ether and dried to give 4-oxo-3,4-dihydro-3-methanesulfonyloxy-1,2,3-benzotriazine (2.6 g), melting point: 132°–134° C. Infrared spectrum: 1720, 1380, 1175 cm$^{-1}$.

Anal. Calcd. for $C_8H_7O_4N_3S$: C, 39.82; H, 2.93; N, 17.42. Found. C, 39.74; H, 2.69; N, 17.39.

EXAMPLE 62

In chloroform (80 ml) are dissolved 1-hydroxy-6-vinyl-1,2,3-benzotriazole (8.0 g) and triethylamine (5.1 g) under stirring, and thereto is added dropwise a solution of methanesulfonyl chloride (5.73 g) in chloroform (20 ml) at a temperature of less than 10° C. The mixture is stirred at room temperature for 1.5 hours. The reaction mixture is washed with water, an aqueous sodium hydrogen carbonate and water in order, dried over anhydrous magnesium sulfate, treated with charcoal and then concentrated till about 40 ml. After dissolving the precipitated crystals by heating, the mixture is allowed to stand. The precipitated crystals are separated by filtration to give 1-methanesulfonyloxy-6-vinyl-1,2,3-benzotriazole (9.1 g), melting point: 129°–129.5° C. The filtrate is concentrated, and the resulting residue is recrystallized from benzene to give additionally the desired product (2.3 g).

Anal. Calcd. for $C_9H_9N_3O_3S$: C, 45.18; H, 3.79; N, 17.56; S, 13.40. Found: C, 45.37; H, 3.58; N, 17.39; S, 13.42.

EXAMPLE 63

In ethyl acetate (50 ml) are dissolved ethyl 2-hydroxyimino-2-cyanoacetate (7.1 g) and triethylamine (7.0 ml). To the solution is added p-toluenesulfonyl chloride (9.5 g) with stirring under ice-cooling, and the mixture is stirred for 2 hours and allowed to stand overnight. The reaction mixture is filtered and the filtrate is concentrated. To the residue is added cyclohexane and the resulting crystals are separated by filtration and dried to give ethyl 2-(p-toluenesulfonyloxyimino)-2-cyanoacetate (13.9 g), melting point: 84°–87° C.

Anal. Calcd. for $C_{12}H_{12}O_5N_2S$: C, 48.64; H, 4.08; N, 9.46. Found: C, 48.63; H, 3.91; N, 9.51.

EXAMPLE 64

In 1 N aqueous sodium hydroxide (45 ml) is dissolved 1-hydroxy-6-nitro-1,2,3-benzotriazole (7.2 g). To the solution is added dropwise benzenesulfonyl chloride (7.0 g) with stirring at room temperature and further are added thereto water (50 ml) and ethyl acetate (100 ml) and the mixture is stirred for 1 hour. The ethyl acetate layer is separated, dried over magnesium sulfate-charcoal, filtered and concentrated until it becomes about 30 ml. n-Hexane (50 ml) is thereto added and the mixture is allowed to stand. The precipitated crystals are separated by filtration and dried to give faint yellow prisms of 1-benzenesulfonyloxy-6-nitro-1,2,3-benzotriazole (6.8 g), melting point: 122°–124° C. The product is recrystallized from ethyl acetate-n-hexane to give a pure product: melting point: 124° C.

Anal. Calcd. for $C_{12}H_8O_5N_4S$: C, 45.01; H, 2.52; N, 17.50. Found: C, 45.12; H, 2.31; N, 17.33.

EXAMPLE 65

In 1 N aqueous sodium hydroxide (45 ml) is dissolved 1-hydroxy-6-nitro-1,2,3-benzotriazole (7.2 g). To the solution is gradually added p-toluenesulfonyl chloride (7.7 g) with stirring under ice-cooling and further are added thereto ethyl acetate (100 ml) and water (50 ml) and the mixture is stirred for 1 hour. The ethyl acetate layer is separated, dried over magnesium sulfate-charcoal, and concentrated until it becomes about 30 ml. n-Hexane (about 50 ml) is added thereto and the mixture is allowed to stand. The precipitated crystals are separated and dried to give faint yellow needles of 1-(p-toluenesulfonyl-oxy)-6-nitro-1,2,3-benzotriazole (7.5 g), melting point: 142°–144° C. The product is recrystallized from ethyl acetate-n-hexane to give a pure product, melting point: 144° C.

Anal. Calcd. for $C_{13}H_{10}O_5N_4S$: C, 46.72; H, 3.02; N, 16.77. Found: C, 46.83; H, 2.80; N, 16.80.

EXAMPLE 66

In 1 N aqueous sodium hydroxide (50 ml) is dissolved 1-hydroxy-6-chloro-1,2,3-benzotriazole (4.5 g) and thereto is added ether (10 ml). To the solution is added benzenesulfonyl chloride (6.0 g) with stirring under ice-cooling and the mixture is stirred at the same temperature for 75 minutes. The reaction mixture is filtered to give crystals. The filtrate is extracted with ethyl acetate (150 ml), and the extract is distilled to remove the solvent. The resulting crystals are combined with those obtained above and recrystallized from benzene-n-hexane to give 1-benzenesulfonyloxy-6-chloro-1,2,3-benzotriazole (6.0 g), melting point: 110°–110.5° C. Infrared spectrum (Nujor): 1200, 1086 cm$^{-1}$.

Anal. Calcd. for $C_{12}H_8N_3O_3SCl$: C, 46.53; H, 2.60; N, 13.57; Cl, 11.45. Found: C, 46.48; H, 2.52; N, 13.54; Cl, 11.52.

EXAMPLE 67

In 1 N aqueous sodium hydroxide (300 ml) is dissolved 1-hydroxy-6-chloro-1,2,3-benzotriazole (38 g) and thereto is added ether (100 ml). To the solution is added dropwise p-chlorobenzenesulfonyl chloride (57 g) with stirring under ice-cooling during 15 minutes, and the mixture is stirred at the same temperature for 70 minutes. The reaction mixture is extracted with ethyl acetate. The extract is washed with a saturated aqueous sodium hydrogen carbonate and water in order and dried over anhydrous magnesium sulfate. After drying, the solvent is distilled off, and the resulting crystals are recrystallized from benzene-petroleum ether to give 1-(p-chlorobenzenesulfonyloxy)-6-chloro-1,2,3-benzotriazole (70.5 g), melting point: 125°–127° C. Infrared spectrum (Nujor): 1190, 1085 cm$^{-1}$.

Anal. Calcd. for $C_{12}H_7N_3O_3SCl_2$: C, 41.88; H, 2.05; N, 12.21. Found: C, 41.84; H, 1.94; N, 12.23.

EXAMPLE 68

In benzene (200 ml) are dissolved 1-hydroxy-6-vinyl-1,2,3-benzotriazole (31.2 g) and triethylamine (20 g) under stirring and thereto is added dropwise a solution of p-vinylbenzenesulfonyl chloride (39.2 g) in benzene (70 ml) under ice-cooling to 10° C. The mixture is stirred at room temperature for 3.5 hours. The reaction mixture is poured onto ice-water (1 liter) and the mixture is extracted with ethyl acetate (500 ml, three times). The combined extracts are washed with an aqueous sodium hydrogen carbonate and then water, dried over anhydrous magnesium sulfate, treated with charcoal, and then concentrated under a reduced pressure till about 150 ml. To the mixture is added n-hexane and the mixture is allowed to stand at a cooled place. The precipitated crystals are separated by filtration to give 1-(p-vinylbenzenesulfonyloxy)-6-vinyl-1,2,3-benzotriazole (28.0 g), melting point: 85°–87° C. To the filtrate is further added n-hexane and the mixture is allowed to stand at a cooled place to give additionally the desired product (11.7 g).

Anal. Calcd. for $C_{16}H_{13}N_3O_3S$: C, 58.70; H, 4.00; N, 12.84. Found: C, 58.70; H, 3.89; N, 12.67.

EXAMPLE 69

In benzene (100 ml) are dissolved 1-hydroxy-6-vinyl-1,2,3-benzotriazole (8.0 g) and triethylamine (5 g) under stirring and thereto is added dropwise a solution of p-chlorobenzenesulfonyl chloride (10.6 g) in benzene (100 ml) under cooling to 10° C. The mixture is stirred at room temperature for 3 hours. The reaction mixture is poured onto ice-water (200 ml) and then extracted with ethyl acetate (150 ml, twice). The combined extracts are washed with water, dried over anhydrous magnesium sulfate, treated with charcoal and then concentrated till about 30 ml. To the mixture is added n-hexane and the mixture is allowed to stand at a cooled place. The precipitated crystals are separated by filtration to give 1-(p-chlorobenzenesulfonyloxy)6-vinyl-1,2,3-benzotriazole (13.9 g), melting point: 125° C. The filtrate is further concentrated and the resulting residue is dissolved in ethyl acetate (10 ml). To the solution is added n-hexane and the mixture is allowed to stand at a cooled place to give additionally the desired product (1.0 g).

Anal. Calcd. for $C_{14}H_{10}N_3O_3SCl$: C, 50.07; H, 3.00; N, 12,51; S, 9.55; Cl, 10.57. Found: C, 50.18; H, 2.93; N, 12.50; S, 9.71; Cl, 10.66.

EXAMPLE 70

In dry benzene (300 ml) are dissolved 1-hydroxy-6-vinyl-1,2,3-benzotriazole (4.83 g) and triethylamine (3.2 g) under stirring, and thereto is added dropwise a solution of p-toluenesulfonyl chloride (5.8 g) in benzene (50 ml) under cooling at 10° C. The mixture is stirred at room temperature for 2 hours. The reaction mixture is poured onto ice-water (200 ml) and extracted with ethyl acetate (60 ml, three times). The combined extracts are washed with an aqueous sodium hydrogen carbonate and then water, dried over anhydrous magnesium sulfate, treated with charcoal and then concentrated under a reduced pressure. The resulting residue is recrystallized from ethyl acetate-n-hexane to give colorless crystals of 1-(p-toluenesulfonyloxy)-6-vinyl-1,2,3-benzotriazole (6.1 g), melting point: 90°–91° C. The filtrate is further concentrated, and the resulting residue is recrystallized from benzene-n-hexane to give additionally the desired product (1.9 g).

Anal. Calcd. for $C_{15}H_{13}N_3O_3S$: C, 57.13; H, 4.16; N, 13.33; S, 10.17. Found: C, 57.37; H, 4.06; N, 13.22; S, 10.37.

EXAMPLE 71

In dry benzene (50 ml) are dissolved 1-hydroxy-6-chloro-1,2,3-benzotriazole (8.5 g) and triethylamine (7.0 ml), and thereto is added p-toluenesulfonyl chloride (9.5 g) at room temperature and the mixture is stirred for 1 hour. To the reaction mixture are added water and benzene. The benzene layer is separated, dried over anhydrous magnesium sulfate and distilled to remove the solvent. The resulting residue is recrystallized from carbon tetrachloride to give 1-(p-toluenesulfonyloxy)-6-chloro-1,2,3-benzotriazole (12.6 g), melting point: 94°–96° C.

Anal. Calcd. for $C_{13}H_{10}N_3O_3SCl$: C, 48.22; H, 3.11; N, 12.98; Cl, 10.95. Found: C, 48.12; H, 2.98; N, 12.82; Cl, 11.43.

EXAMPLE 72

In water (20 ml) are dissolved 4-oxo-3,4-dihydro-3-hydroxy-1,2,3-benzotriazine (2.4 g) and sodium hydrogen carbonate (1.3 g), and thereto is added a solution of benzenesulfonyl chloride (2.65 g) in ethyl acetate (20 ml) under ice-cooling and the mixture is stirred for 2 hours. The precipitated crystals are separated by filtration. The ethyl acetate layer is separated from the filtrate and concentrated. The resulting crystals are separated by filtration and combined with the crystals obtained above. The crystals are washed with ether, dried and then recrystallized from benzene to give 4-oxo-3,4-dihydro-3-benzene-sulfonyloxy-1,2,3-benzotriazine (4.0 g), melting point: 132°–134° C. Infrared spectrum: 1705, 1390, 1195 cm$^{-1}$.

EXAMPLE 73

In 1 N aqueous sodium hydroxide (b 98 ml) is dissolved 1-hydroxy-1,2,3-benzotriazole (13.5 g). To the solution is added powdery p-nitrobenzenesulfonyl chloride (22.2 g) with stirring under ice-cooling, and the mixture is stirred at the same temperature for 15 minutes and further at room temperature for 4.5 hours. After allowing to stand overnight, the reaction mixture is extracted with ethyl acetate (150 ml). The extract is washed with water and dried over anhydrous sodium sulfate. After drying, the solvent is distilled off. The resulting powdery residue is washed twice with petroleum ether (30 ml) and recrystallized from benzene (90 ml) to give colorless crystals. The crystals are dissolved in ethyl acetate (100 ml) and the mixture is washed twice with a saturated aqueous sodium hydrogen carbonate (10 ml) and water in order and dried over anhydrous sodium sulfate. After drying, the solvent is distilled off under a reduced pressure to give colorless crystals of 1-(p-nitrobenzensulfonyloxy)-1,2,3-benzotriazole (14 g), melting point: 119.5°–121.5° C. Ultraviolet spectrum (methanol): λmax 254 nm, E=234.

Anal. Calcd. for $C_{12}H_8O_5N_4S$: C,45.00; H,2.52; N,17.49. Found: C,44,88; H,2.35; N,16.94.

EXAMPLE 74

In benzene (40 ml) are dissolved 1-hydroxy-1,2,3-benzotriazole (10.6 g) and triethylamine (11.1 ml). To the solution is added dropwise a solution of p-chlorobenzenesulfonyl chloride (16.6 g) in benzene (8 ml) with stirring under ice-cooling during about 20 minutes, and the mixture is stirred at 15° C. for 4 hours. To the reaction mixture is added water and the benzene layer is separated. The aqueous layer is extracted twice with ethyl acetate (100 ml). The extract is combined with the above benzene layer, washed with a small amount of an aqueous sodium hydrogen carbonate and water in order and dried over anhydrous sodium sulfate. After drying, the solvent is distilled off under a reduced pressure. The resulting crystals are cracked in petroleum ether and separated by filtration and dried to give faint yellow crystals of 1-(p-chlorobenzensulfonyloxy)-1,2,3-benzotriazole (21.2 g), melting point: 94°–95° C. Ultraviolet spectrum (methanol): λmax 224 mμ, E=365.

Anal. Calcd. for $C_{12}H_8O_3N_3SCl$: C,46.49; H,2.62; N,13.56. Found: C,46.65; H,2.46; N,13.85.

EXAMPLE 75

In 1 N aqueous sodium hydroxide (49 ml) is dissolved 1-hydroxy-1,2,3-benzotriazole (6.6 g) (pH 6.8). To the solution is added dropwise benzenesulfonyl chloride (8.8 g) with stirring under ice-cooling and the mixture is stirred for 1 hour. The reaction mixture is extracted with ethyl acetate and the extract is washed with water and dried over anhydrous magnesium sulfate. After drying, the solvent is distilled off. The crystalline residue is cracked well in n-hexane and separated by filtration and dried to give 1-benzenesulfonyloxy-1,2,3-benzotriazole (11.5 g), melting point: 83°–84° C.

Anal. Calcd. for $C_{12}H_9O_3N_3S$: C,52.35; H,3.30; N,15.27. Found: C,52.30; H,3.09; N,15.13.

EXAMPLE 76

In dichloromethane (70 ml) are added 1-hydroxy-1,2,3-benzotriazole (3.4 g) and further triethylamine (3.7 ml). To the solution is added dropwise a solution of 2,4,6-trimethylbenzenesulfonyl chloride (4.5 g) is dichloromethane (20 ml) at room temperature, and the mixture is stirred for 1 hour. The reaction mixture is washed with water and dried over anhydrous magnesium sulfate, and the solvent is distilled off. The resulting residue is washed with ethyl acetate-n-hexane (1:1; 50 ml) and dried to give colorless crystals of 1-(2,4,6-trimethylbenzenesulfonyloxy)-1,2,3-benzotriazole (5.5 g), melting point: 128°–130° C. The product is recrystallized from dichloromethane-n-hexane to give colorless prisms, melting point: 130°–131° C.

Anal. Calcd. for $C_{15}H_{15}O_3N_3S$: C,56.76; L H,4.76; N,13.25. Found: C,56.72; H,4.71; N,13.02.

What is claimed is:

1. A sulfonic acid ester of the formula:

wherein $R_1'$ is a member selected from the group consisting of alkyl having 1 to 6 carbon atoms, oxo substituted bicycloalkylalkyl having 7 to 10 carbon atoms in the bicycloalkyl moiety and having 1 to 6 carbon atoms in the alkyl moiety, phenylalkyl having 1 to 6 carbon atoms in the alkyl moiety, phenylalkenyl having 2 to 6 carbon atoms in the alkenyl moiety, phenyl, 2,4,6-trimethylphenyl, alkylphenyl having one alkyl having 1 to 6 carbon atoms in the alkyl group thereof, phenyl having 1 to 3 substituent(s) selected from the group consisting of alkenyl having 2 to 6 carbon atoms, halogen, and nitro, and β-pyridyl, and $R_2'O—$ is a member selected from the group consisting of benzotriazolyloxy, benzotriazolyloxy having one substituent selected from the group consisting of nitro, halogen and alkenyl having 2 to 6 carbon atoms, and oxo substituted dihydrobenzotriazinyloxy, with the proviso that when $R_1'$ is phenyl having one alkyl, $R_2'O—$ is not benzotriazolyloxy.

2. A compound of claim 1, wherein $R_1'$ is a member selected from the group consisting of alkyl having 1 to 6 carbon atoms, oxo substituted bicycloalkylalkyl having 7 to 10 carbon atoms in the bicycloalkyl moiety and having 1 to 6 carbon atoms in the alkyl moiety, phenylalkyl having 1 to 6 carbon atoms in the alkyl moiety, phenyl alkylphenyl having one alkyl having 1 to 6 carbon atoms in the alkyl group thereof, and phenyl having 1 to 3 substituent(s) selected from the group consisting of alkenyl having 2 to 6 carbon atoms, halogen and nitro and $R_2'O—$ is a member selected from the group consisting of benzotriazolyloxy and benzotriazolyloxy having one substituent selected from the group consisting of nitro, halogen and alkenyl having 2 to 6 carbon atoms.

3. A compound of claim 2, wherein $R_1'$ is a member selected from the group consisting of alkyl having 1 to 6 carbon atoms, oxo substituted bicycloalkylalkyl having 7 to 10 carbon atoms in the bicycloalkyl moiety and having 1 to 6 carbon atoms in the alkyl moiety, phenylalkyl having 1 to 6 carbon atoms in the alkyl moiety, phenyl, and phenyl having one substituent selected from the group consisting of alkenyl having 2 to 6 carbon atoms, halogen and nitro.

4. A compound of claim 3, wherein $R_1'$ is a member selected from the group consisting of alkyl having 1 to 6 carbon atoms, oxo substituted, bicycloalkylalkyl having 7 to 10 carbon atoms in the bicycloalkyl moiety and having 1 to 6 carbon atoms in the alkyl moiety and phenylalkyl having 1 to 6 carbon atoms in the alkyl moiety.

5. A compound of claim 4, wherein $R_1'$ is alkyl having 1 to 6 carbon atoms.

6. A compound of claim 5, wherein $R_1'$ is a member selected from the group consisting of methyl and n-butyl and $R_2'O-$ is a member selected from the group consisting of benzotriazolyloxy and benzotriazolyloxy having one substituent selected from the group consisting of nitro, chlorine, and vinyl.

7. A compound of claim 4, wherein $R_1'$ is oxo substituted bicycloalkylalkyl having 7 to 10 carbon atoms in the bicycloalkyl moiety and having 1 to 6 carbon atoms in the alkyl moiety and $R_2'O-$ is a member selected from the group consisting of benzotriazolyloxy and benzotriazolyloxy having one substituent selected from the group consisting of nitro and halogen.

8. A compound of claim 7, wherein $R_1'$ is 2-oxo-10-camphyl and $R_2'O-$ is a member selected from the group consisting of benzotriazolyloxy and benzotriazolyloxy having one substituent selected from the group consisting of nitro and chlorine.

9. A compound of claim 4, wherein $R_1'$ is phenylalkyl having 1 to 6 carbon atoms in the alkyl moiety and $R_2'O-$ is a member selected from the group consisting of benzotriazolyloxy and benzotriazolyloxy having one halogen.

10. A compound of claim 9, wherein $R_1'$ is benzyl and $R_2'O-$ is a member selected from the group consisting of benzotriazolyloxy and benzotriazolyloxy having one chlorine.

11. A compound of claim 3, wherein $R_1'$ is a member selected from the group consisting of phenyl and phenyl having one substituent selected from the group consisting of alkenyl having 2 to 6 carbon atoms, halogen and nitro.

12. A compound of claim 11, wherein $R_1'$ is phenyl and $R_2'O-$ is a member selected from the group consisting of benzotriazolyloxy and benzotriazolyloxy having one substituent selected from the group consisting of nitro and halogen.

13. A compound of claim 12, wherein $R_2'O-$ is a member selected from the group consisting of benzotriazolyloxy and benzotriazolyloxy having one substituent selected from the group consisting of nitro and chlorine.

14. A compound of claim 11, wherein $R_1'$ is phenyl having one alkenyl having 2 to 6 carbon atoms and $R_2'O-$ is benzotriazolyloxy having one alkenyl having 2 to 6 carbon atoms.

15. A compound of claim 14, wherein $R_1'$ is phenyl having one vinyl and $R_2'O-$ is benzotriazolyloxy having one vinyl.

16. A compound of claim 11, wherein $R_1'$ is phenyl having one halogen and $R_2'O-$ is a member selected from the group consisting of benzotriazolyloxy and benzotriazolyloxy having one substituent selected from the group consisting of alkenyl having 2 to 6 carbon atoms and halogen.

17. A compound of claim 16, wherein $R_1'$ is phenyl having one chlorine and $R_2'O-$ is a member selected from the group consisting of benzotriazolyloxy and benzotriazolyloxy having one substituent selected from the group consisting of vinyl and chlorine.

18. A compound of claim 2, wherein $R_1'$ is phenyl having one alkyl having 1 to 6 carbon atoms and $R_2'O-$ is benzotriazolyloxy having one substituent selected from the group consisting of nitro, halogen and alkenyl having 2 to 6 carbon atoms.

19. A compound of claim 18, wherein $R_1'$ is phenyl having one methyl and $R_2'O-$ is benzotriazolyloxy having one substituent selected from the group consisting of nitro, chlorine and vinyl.

20. A compound of claim 1, wherein $R_1'$ is phenylalkenyl having 2 to 6 carbon atoms in the alkenyl moiety and $R_2'O-$ is benzotriazolyloxy.

21. A compound of claim 1, wherein $R_1'$ is a member selected from the group consisting of alkyl having 1 to 6 carbon atoms and phenyl and $R_2'O-$ is oxo substituted dihydrobenzotriazinyloxy.

22. A compound of claim 6, wherein $R_2'O-$ is a member selected from the group consisting of 1,2,3-benzotriazol-1-yloxy, 6-nitro-1,2,3-benzotriazol-1-yloxy, 4-chloro-1,2,3-benzotriazol-1-yloxy, 6-chloro-1,2,3-benzotriazol-1-yloxy and 6-vinyl-1,2,3-benzotriazol-1-yloxy.

23. A compound of claim 22, wherein $R_1'$ is methyl and $R_2'O-$ is 1,2,3-benzotriazol-1-yloxy.

24. A compound of claim 22, wherein $R_1'$ is a methyl and $R_2'O-$ is 6-nitro-1,2,3-benzotriazol-1-yloxy.

25. A compound of claim 22, wherein $R_1'$ is methyl and $R_2'O-$ is 4-chloro-1,2,3-benzotriazol-1-yloxy.

26. A compound of claim 22, wherein $R_1'$ is methyl and $R_2'O-$ is 6-chloro-1,2,3-benzotriazol-1-yloxy.

27. A compound of claim 22, wherein $R_1'$ is n-butyl and $R_2'O-$ is 1,2,3-benzotriazol-1-yloxy.

28. A compound of claim 22, wherein $R_1'$ is n-butyl and $R_2'O-$ is 6-chloro-1,2,3-benzotriazol-1-yloxy.

29. A compound of claim 22, wherein $R_1'$ is methyl and $R_2'O-$ is 6-vinyl-1,2,3-benzotriazol-1-yloxy.

30. A compound of claim 8, wherein $R_1'$ is DL-2-oxo-10-camphyl and $R_2'O-$ is a member selected from the group consisting of 1,2,3-benzotriazol-1-yloxy, 6-nitro-1,2,3-benzotriazol-1-yloxy and 6-chloro-1,2,3-benzotriazol-1-yloxy.

31. A compound of claim 30, wherein $R_2'O-$ is 1,2,3-benzotriazol-1-yloxy.

32. A compound of claim 30, wherein $R_2'O-$ is 6-nitro-1,2,3-benzotriazol-1-yloxy.

33. A compound of claim 30, wherein $R_2'O-$ is 6-chloro-1,2,3-benzotriazol-1-yloxy.

34. A compound of claim 10, wherein $R_2'O-$ is a member selected from the group consisting of 1,2,3-benzotriazol-1-yloxy and 6-chloro-1,2,3-benzotriazol-1-yloxy.

35. A compound of claim 34, wherein $R_2'O-$ is 1,2,3-benzotriazol-1-yloxy.

36. A compound of claim 34, wherein $R_2'O-$ is 6-chloro-1,2,3-benzotriazol-1-yloxy.

37. A compound of claim 13, wherein $R_2'O-$ is a member selected from the group consisting of 1,2,3-benzotriazol-1-yloxy, 6-nitro-1,2,3-benzotriazol-1-yloxy and 6-chloro-1,2,3-benzotriazol-1-yloxy.

38. A compound of claim 37, wherein $R_2'O-$ is 1,2,3-benzotriazol-1-yloxy.

39. A compound of claim 37, wherein $R_2'O-$ is 6-nitro-1,2,3-benzotriazol-1-yloxy.

40. A compound of claim 37, wherein $R_2'O-$ is 6-chloro-1,2,3-benzotriazol-1-yloxy.

41. A compound of claim 1, wherein $R_1'$ is 2,4,6-trimethylphenyl and $R_2'O-$ is 1,2,3-benzotriazol-1-yloxy.

42. A compound of claim 15, wherein $R_1'$ is p-vinylphenyl and $R_2'O-$ is 6-vinyl-1,2,3-benzotriazol-1-yloxy.

43. A compound of claim 17, wherein $R_1'$ is p-chlorophenyl and $R_2'O-$ is a member selected from the group consisting of 1,2,3-benzotriazol-1-yloxy, 6-vinyl-1,2,3-benzotriazol-1-yloxy and 6-chloro-1,2,3-benzotriazol-1-yloxy.

44. A compound of claim 43, wherein $R_2'O-$ is 1,2,3-benzotriazol-1-yloxy.

45. A compound of claim 43, wherein $R_2'O-$ is 6-vinyl-1,2,3-benzotriazol-1-yloxy.

46. A compound of claim 43, wherein $R_2'O-$ is 6-chloro-1,2,3-benzotriazol-1-yloxy.

47. A compound of claim 11, wherein $R_1'$ is phenyl having one nitro and $R_2'O-$ is benzotriazolyloxy.

48. A compound of claim 47, wherein $R_1'$ is p-nitrophenyl and $R_2'O-$ is 1,2,3-benzotriazol-1-yloxy.

49. A compound of claim 19, wherein $R_1'$ is p-tolyl and $R_2'O-$ is a member selected from the group consisting of 6-nitro-1,2,3-benzotriazol-1-yloxy, 6-chloro-1,2,3-benzotriazol-1-yloxy and 6-vinyl-1,2,3-benzotriazol-1-yloxy.

50. A compound of claim 49, wherein $R_2'O-$ is 6-nitro-1,2,3-benzotriazol-1-yloxy.

51. A compound of claim 49, wherein $R_2'O-$ is 6-chloro-1,2,3-benzotriazol-1-yloxy.

52. A compound of claim 49, wherein $R_2'O-$ is 6-vinyl-1,2,3-benzotriazol-1-yloxy.

53. A compound of claim 20, wherein $R_1'$ is β-styryl and $R_2'O-$ is 1,2,3-benzotriazol-1-yloxy.

54. A compound of claim 1, wherein $R_1'$ is 3-pyridyl and $R_2'O-$ is 1,2,3-benzotriazol-1-yloxy.

55. A compound of claim 21, wherein $R_1'$ is a member selected from the group consisting of methyl and phenyl and $R_2'O-$ is 4-oxo-3,4-dihydro-1,2,3-benzotriazin-3-yloxy.

56. A compound of claim 55, wherein $R_1'$ is methyl.

57. A compound of claim 55, wherein $R_1'$ is phenyl.

* * * * *